(12) United States Patent
Saikumar et al.

(10) Patent No.: US 10,398,661 B2
(45) Date of Patent: Sep. 3, 2019

(54) METHODS FOR CLASSIFYING A CANCER AS SUSCEPTIBLE TO TMEPAI-DIRECTED THERAPIES AND TREATING SUCH CANCERS

(71) Applicant: THE BOARD OF REGENTS OF THE UNIVERSITY OF TEXAS SYSTEM, Austin, TX (US)

(72) Inventors: Pothana Saikumar, San Antonio, TX (US); Prajjal Kanti Singha, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/769,504

(22) PCT Filed: Feb. 26, 2014

(86) PCT No.: PCT/US2014/018709
§ 371 (c)(1),
(2) Date: Aug. 21, 2015

(87) PCT Pub. No.: WO2014/134179
PCT Pub. Date: Sep. 4, 2014

(65) Prior Publication Data
US 2016/0000735 A1    Jan. 7, 2016

Related U.S. Application Data

(60) Provisional application No. 61/770,723, filed on Feb. 28, 2013.

(51) Int. Cl.
| | |
|---|---|
| G01N 33/574 | (2006.01) |
| A61K 31/19 | (2006.01) |
| A61K 45/06 | (2006.01) |
| C12N 15/113 | (2010.01) |
| C12Q 1/6886 | (2018.01) |
| A61K 39/00 | (2006.01) |

(52) U.S. Cl.
CPC .............. *A61K 31/19* (2013.01); *A61K 45/06* (2013.01); *C12N 15/1138* (2013.01); *C12Q 1/6886* (2013.01); *G01N 33/57415* (2013.01); *G01N 33/57484* (2013.01); *A61K 2039/505* (2013.01); *C12N 2310/531* (2013.01); *C12N 2320/30* (2013.01); *C12Q 2600/106* (2013.01); *C12Q 2600/158* (2013.01); *G01N 2333/4704* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2008/0118462 A1 | 5/2008 | Alani et al. | |
| 2009/0258096 A1* | 10/2009 | Cohen | A61K 36/483 424/769 |
| 2011/0263693 A1 | 10/2011 | Vinson-Hieronymus et al. | |
| 2011/0301054 A1* | 12/2011 | Bjourson | C12Q 1/6886 506/9 |

FOREIGN PATENT DOCUMENTS

WO    WO 2012/027723    3/2012

OTHER PUBLICATIONS

Hieronymus et al. Cancer Cell 10, 321-330, Oct. 2006.*
Extended European Search Report issued in European Patent Application No. 14757801.7, dated Jul. 18, 2016.
Liu et al., "PMEPA1 promotes androgen receptor-negative prostate cell proliferation through suppressing the Smad3/4-c-Myc-p21 Cip1 signaling pathway," *Journal of Pathology*, 223:683-694, 2011.
Bai et al., "TMEPAI inhibits TGF-β signaling by promoting lysosome degradation of TGF-β receptor and contributes to lung cancer development," *Cell Signal.*, (9):2030-9, 2014.
Bonafoux et al., "Strategies for TGF-beta modulation: a review of recent patents," *Expert Opin. Ther. Pat.*, 19(12):1759-69, 2009.
Brunschwig et al., "PMEPA1, a transforming growth factor-beta-induced marker of terminal colonocyte differentiation whose expression is maintained in primary and metastatic colon cancer," *Cancer Res.*, 63:1568-75, 2003.
Cichon and Radisky, "Cutting the brakes and flooring the gas: how TMEPAI turns TGF-β into a tumor promoter," *Genes Cancer*, 5(9-10):303-5, 2014.
Györffy et al., "An online survival analysis tool to rapidly assess the effect of 22,277 genes on breast cancer prognosis using microarray data of 1,809 patients," *Breast Cancer Res Treat.*, 123(3):725-31, 2010.
Kang et al., "New regulatory mechanisms of TGF-beta receptor function," *Trends Cell Biol.*, 19:385-94, 2009.
Moustakas et al., "Non-Smad TGF-beta singals," *J. Cell Sci.*, 118:3573-84, 2005.
Parvani et al., "Noncanonical TGF-beta signaling mammary tumorignesis," *J. Mammary Gland Biol. Neoplasia*, 16(2):127-46, 2011.
PCT International Search Report and Written Opinion issued in International Patent Application No. PCT/US2014/018709, dated May 12, 2014.
Samarnthai et al., "TMEPAI Gene Amplification in Triple Negative Breast Cancers," *Mod. Pathol.*, 23:70A, 2010.
Singha et al., "PS-11-04: TMEPAI is a feedback regulator of TGF-b signaling during breast cancer progression," *Cancer Research*, 71(24):P2-11-04, 2011.

(Continued)

Primary Examiner — Bong-Sook Baek
(74) Attorney, Agent, or Firm — Parker Highlander PLLC

(57) ABSTRACT

The invention provides methods for classifying a cancer as susceptible to transmembrane prostate androgen induced (TMEPAI)-directed therapies, and methods for treating such cancers. The field of the invention pertains generally to medicine, pathology and oncology. More particularly, it addresses the treatment of breast cancer, such as triple-negative breast cancer, using a transmembrane prostate androgen induced (TMEPAI)-directed therapy.

8 Claims, 16 Drawing Sheets

(56) References Cited

OTHER PUBLICATIONS

Singha et al., "TGF-β induced TMEPAI/PMEPA1 inhibits canonical Smad signaling through R-Smad sequestration and promotes non-canonical PI3K/Akt signaling by reducing PTEN in triple negative breast cancer," *Genes Cancer*, 5(9-10):320-36, 2014.
Singha et al., "Transforming growth factor-beta (TGF-beta)-inducible gene TMEPAI converts TGF-beta from a tumor suppressor to a tumor promoter in breast cancer," *Cancer Res*earch, 70(15):6377-6383, 2010.
Vo Nguyen et al., "TMEPAI/PMEPA1 enhances tumorigenic activities in lung cancer cells," *Cancer Sci.*, 105(3):334-41, 2014.
Watanabe et al. TMEPAI, a transmembrane TGF-β-inducible protein, sequesters Smad proteins from active participation in TGF-β signaling. *Mol Cell*; 37(1):123-34, 2010.
Xu et al., "A novel androgen-regulated gene, PMEPA1, located on chromosome 20q13 exhibits high level expression in prostate," *Genomics*, 66(3):257-63, 2000. Erratum in: *Genomics*, 70:4007, 2000.

* cited by examiner

METHODS FOR CLASSIFYING A CANCER AS SUSCEPTIBLE TO TMEPAI-DIRECTED THERAPIES AND TREATING SUCH CANCERS

This application is a national phase application under 35 U.S.C. § 371 of International Application No. PCT/US2014/018709, filed Feb. 26, 2014, which claims benefit of priority to U.S. Provisional Application Ser. No. 61/770,723, filed Feb. 28, 2013. The entire contents of the above-referenced disclosures are specifically incorporated herein by reference.

BACKGROUND OF THE INVENTION

1. Field of the Invention

The field of the invention pertains generally to medicine, pathology and oncology. More particularly, it addresses the treatment of breast cancer, such as triple-negative breast cancer, using a transmembrane prostate androgen induced (TMEPAI)-directed therapy.

2. Related Art

Although triple-negative breast cancers (TNBC) represent a relatively small percentage (15-25%) of total breast cancer cases, it is responsible for a disproportionately higher number of breast cancer deaths with shorter recurrence times and fewer therapeutic options in young women and minorities. TNBCs are negative for estrogen receptor (ER), progesterone receptor (PR), and human epidermal growth factor receptor 2 (HER2) and are characterized by frequent ductal involvement, high grade, and high growth rates. Despite advances in treatment of ER-positive and HER2-positive breast cancers, there has been less progress in the treatment of ER-negative TNBC due to lack of focused targets that critically determine their growth, invasion and metastasis.

So far in the literature and patents the focus has been to inhibit TGF-β/Smad signaling as a therapeutic approach (see Bonafoux & Lee, 2009). In contrast, the inventors' prior studies exploited the dependency of TNBC on TGF-β for their growth, invasion and metastasis. They hypothesized that genes implied in bypassing replicative senescence caused by TGF-β could be "missing links" involved in converting TGF-β from tumor suppressor to tumor promoter (TGF-β paradox). Since amplification of Chr20q13 in cancer is often associated with immortalization and escape from cell senescence, they focused on a TGF-β inducible gene that is located at Chr20q13, TMEPAI (transmembrane prostate androgen induced). Strikingly, TMEPAI showed gene amplification in 47 of 97 breast cancers (48.5%), including 45/85 (53%) invasive ductal carcinomas and 2/11 (18%) invasive lobular carcinomas. The majority of tumors (72.3%) with TMEPAI copy number gain were of histologic grade 3 (34/47). Among 31 TNBCs, TMEPAI was amplified in 18 (58.1%) of them. The inventors' previous work suggests that amplified TMEPAI promotes TNBC growth and invasion, and that TMEPAI gene knockdown corrects the aggressive behavior of a prototypic TNBC (1).

SUMMARY OF THE INVENTION

Thus, in accordance with the present invention, there is provided a method of inhibiting a cancer cell that overexpresses transmembrane prostate androgen induced (TMEPAI) compared to normal control cell comprising contacting the cancer cell with an agent that inhibits TMEPAI expression or activity. The cancer cell may be selected from a brain cancer cell, a prostate cancer cell, a lung cancer cell, a head & neck cancer cell, a esophageal cancer cell, a pancreatic cancer cell, a stomach cancer cell, a liver cancer cell, a colon cancer cell, a ovarian cancer cell, a cervical cancer cell, a testicular cancer cell, or a skin cancer cell. The cancer cell may be a breast cancer cell, such as a triple-negative breast cancer cell. The agent may be an siRNA or an antisense molecule, an intrabody, or a small molecule, such as a triterpenoid. The method may further comprise contacting said cell with a second anti-cancer agent or therapy. The cancer cell may be metastatic, recurrent or multi-drug resistant. The agent may be embedded in or coated on a nanoparticle.

In another embodiment, there is provided a method of treating a subject with cancer, wherein cells of said cancer overexpress transmembrane prostate androgen induced (TMEPAI) compared to normal cells, said method comprising administering to subject an agent that inhibits TMEPAI expression or activity. The cancer cell may be selected from a brain cancer cell, a prostate cancer cell, a lung cancer cell, a head & neck cancer cell, a esophageal cancer cell, a pancreatic cancer cell, a stomach cancer cell, a liver cancer cell, a colon cancer cell, a ovarian cancer cell, a cervical cancer cell, a testicular cancer cell, or a skin cancer cell. The cancer cell may be a breast cancer cell, such as a triple-negative breast cancer cell. The agent may be an siRNA or an antisense molecule, an intrabody, or a small molecule, such as a triterpenoid. The cancer cell may be metastatic, recurrent or multi-drug resistant. The agent may be embedded in or coated on a nanoparticle.

The method may further comprise contacting said cell with a second anti-cancer agent or therapy. The second anti-cancer agent may be delivered before said agent, after said agent, or at the same time as said agent. The method may also further comprise measuring TMEPAI levels in a cancer cell from said subject. The agent may be administered intravenously, intra-arterially, subcutaneously, or orally, or the agent may be administered intratumorally, local or regional to a tumor site, or systemically. The agent may administered more than once. The subject may be a human subject. Treating may result in one or more of reduced tumor burden, slowing of tumor growth, increased length of survival, rendering an unresectable tumor resectable, or improvement of quality of life. The method may further comprise obtaining information on TMEPAI expression in a cancer cell from said subject, such as by obtaining a cancer cell or tissue biopsy and assessing TMEPAI mRNA levels, or by obtaining a cancer cell or tissue biopsy and assessing TMEPAI protein levels. The information may be obtained prior to treatment with said agent, or after treatment with said agent, or both.

Also provided is a method for classifying a patient as benefiting from TMEPAI inhibitory therapy comprising a) obtaining a sample from a cancer patient, wherein said sample comprises a cancer cell; and b) assessing TMEPAI levels in said patient, wherein an increased level of TMEPAI in a cancer cell form said sample indicates that said patient will benefit from TMEPAI inhibitory therapy. The cancer cell may be selected from a brain cancer cell, a prostate cancer cell, a lung cancer cell, a head & neck cancer cell, a esophageal cancer cell, a pancreatic cancer cell, a stomach cancer cell, a liver cancer cell, a colon cancer cell, a ovarian cancer cell, a cervical cancer cell, a testicular cancer cell, or a skin cancer cell. The breast cancer cell may a triple-negative breast cancer cell. The method may further comprise treating said patient with a) an agent that inhibits TMEPAI expression or activity, and/or b) a TGF-β-based therapy.

In addition, there is provided a method for monitoring a cancer therapy in a patient comprising a) obtaining a sample from a cancer patient undergoing cancer therapy, wherein said sample comprises a cancer cell; b) assessing TMEPAI levels in said cancer cell; and c) comparing levels in said cancer cell as compared to a pretreatment or earlier assessed TMEPAI level, wherein an decreased level of TMEPAI in a cancer cell form said sample indicates that said patient is benefiting from said cancer therapy. The cancer cell may be selected from a brain cancer cell, a prostate cancer cell, a lung cancer cell, a head & neck cancer cell, a esophageal cancer cell, a pancreatic cancer cell, a stomach cancer cell, a liver cancer cell, a colon cancer cell, a ovarian cancer cell, a cervical cancer cell, a testicular cancer cell, or a skin cancer cell. The breast cancer cell may a triple-negative breast cancer cell. The therapy may be a) an agent that inhibits TMEPAI expression or activity, and/or b) a TGF-β-based therapy.

Also provided is a method for classifying a patient as benefiting from TMEPAI inhibitory therapy comprising (a) obtaining a blood, plasma or serum sample from a cancer patient; and (b) assessing TMEPAI levels in said blood, plasma or serum sample, wherein an increased level of TMEPAI in said blood, plasma or serum sample indicates that said patient will benefit from TMEPAI inhibitory therapy. The method may further comprise treating the subject with an agent that inhibits TMEPAI expression or activity, and/or a TGF-β-based therapy.

A further embodiment comprises a method for monitoring a cancer therapy in a patient comprising (a) obtaining a blood, plasma or serum sample from a cancer patient undergoing cancer therapy; (b) assessing TMEPAI levels in said blood, plasma or serum sample; and (c) comparing levels in said blood, plasma or serum sample as compared to a pretreatment or earlier assessed TMEPAI level, wherein a decreased level of TMEPAI in a blood, plasma or serum sample said sample indicates that said patient is benefiting from said cancer therapy. The method may further comprise treating the subject with an agent that inhibits TMEPAI expression or activity, and/or a TGF-β-based therapy.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIG. 1A. Effect of TGF-β on TMEPAI mRNA expression by QPCR in normal human mammary epithelial (HMEC) and MDA-MB-231 breast cancer cells, which is inhibited by TGF-β receptor I kinase inhibitor SB431542 (SB). FIG. 1B. Relative expression of TMEPAI protein in HMEC and MDA-MB-231 cells without or with TGF-β stimulation.

FIG. 3A. TMEPAI protein levels in various breast tumors were analyzed by immunohistochemistry (IHC). FIG. 3B. Comparison of gene amplification by array comparative genomic hybridization (aCGH) and protein expression by IHC in 17 different breast tumors.

FIG. 4A. Triple-negative BT-20, MDA-MB-231 and HCC1937 breast cancer cells were transiently transfected with 12XCAGA-Luc and TMEPAI or control expression constructs. Cells were treated with or without TGF-β (2 ng/ml) for 16 h. —Fold change in relative light units (RLU) of Firefly Luciferase activity normalized with Renilla luciferase activity is presented as mean±SD from three transfections. Asterisk denotes p<0.001 for pcDNA vs. pTMEPAI in presence of TGF-β. FIG. 4B. Effect of TMEPAI knockdown on Smad signaling in MDA-MB-231 cells measured by 12xCAGA-Luc reporter activity and presented as RLU normalized as described above. Inset shows relative expression of TMEPAI in two different clones stably expressing two different shRNAs (ShRNA1 and shRNA2). Asterisk denotes p<0.001 for CON shRNA vs TMEPAI shRNA in presence of TGF-β. FIG. 4C. Western blots for phosphorylated and total Smad2 and Smad3, Smad4, Smad7, TMEPAI and GAPDH proteins in MDA-MB-231 cells expressing control or TMEPAI shRNA. Cells were incubated without or with 2 ng/ml TGF-β FIG. 4D. —Fold change in relative light units (RLU) of normalized 12XCAGA driven firefly-luciferase activity in HMEC and breast cancer cell lines expressing control shRNA (MDA-MB-231) or TMEPAI shRNA (231-TMKD) in the absence or presence of TGF-β. Human TMEPAI gene was expressed in HMEC and MDA-MB-231 cells, mouse TMEPAI was expressed in 231-TMKD cells. Asterisk denotes p<0.001 for pcDNA vs pTMEPAI in presence of TGF-β. FIG. 4E. Western blots for phosphorylated and total Smad2/3 in HMEC expressing control pcDNA or pTMEPAI in the absence or presence of TGF-β. FIG. 4F. —Fold change in normalized 12xCAGA-Luc reporter activity in HCC1937 cells expressing control and TMEPAI shRNA and treated without or with TGF-β. Asterisk denotes p<0.001 for CON shRNA vs TMEPAI shRNA in presence of TGF-β. FIG. 4G. Growth curves of HCC1937 cells expressing control and TMEPAI shRNA (HCC1937 and HCC1937_TMEPAI_KD, respectively) in the absence or presence of TGF-β. FIG. 4H. Relative expression of Smad signaling molecules, Smad2, pSmad2, Smad3, pSmad3, Smad4, Smad7 and TMEPAI in HCC1937 cells expressing control or TMEPAI shRNA.

FIG. 5A. Relative expression of PTEN, phosphorylated Akt (pAkt), total Akt, p21, p27 and GAPDH in MDA-MB-231 cells expressing control (CON shRNA) or TMEPAI shRNA by Western blotting. Reducing the expression of TMEPAI by shRNA leads to increased PTEN, p27 and p21 along with decreased pAkt in MDA MB-231 breast cancer cells. FIG. 5B. Relative expression of PTEN, pAkt, total Aid, p21, p27 and Tubulin in HCC1937 cells expressing control or TMEPAI shRNA. Again, in HCC1937, another triple-negative breast cancer line, reduction of TMEPAI levels leads to increased PTEN, p27 and p21 protein levels and decreased pAkt. FIG. 5C. Relative expression of PTEN, pAkt, total Aid, p21, p27 and GAPDH in HMEC expressing control (pcDNA) or TMEPAI (pTMEPAI) vectors by Western blotting. Forced expression of TMEPAI in normal mammary epithelial cells results in decreased PTEN, p27 and P21 along with increased pAkt.

FIG. 7A. Ductal breast carcinoma in situ show ~6-fold increase in TMEPAI mRNA expression relative to normal breast. FIG. 7B. Lung adenocarcinomas show ~2.6-fold increase in TMEPAI mRNA over normal Lung. FIG. 7C. Pancreatic ductal carcinomas show ~3-fold increase in TMEPAI expression. FIG. 7D. Rectosigmoid adenocarcinomas show ~4-fold increase in TMEPAI expression over normal colon. Numbers in parenthesis indicate number of samples.

FIG. 8A. Reduced breast tumorigenic potential in vivo of TMEPAI knockdown cells as measured by tumor volume (*P<0.05). Inset shows representative tumors. FIG. 8B. Reduced expression of VEGF and Ki67 in tumors formed by TMEPAI knockdown cells compared to cells expressing control shRNA. FIG. 8C. Relative expression of HIF-1α in control and TMEPAI knockdown cells and xenograft breast tumors. HeLa cells treated with cobalt chloride were used as positive control for HIF-1α expression. FIG. 8D. Expression of pAkt, PTEN, p27$^{kip1}$ and HIF-1α and TMEPAI in cells expressing control shRNA and TMEPAI shRNA.

FIG. 9A-B. Relative expression of Snail and TMEPAI protein (FIG. 9A) and mRNA (FIG. 9B) in MDA-MB-231 cells expressing control (CON) or TMEPAI shRNA in the absence or presence of TGF-β. Asterisk denotes p<0.001 for Control shRNA vs. TMEPAI shRNA in presence of TGF-β. FIG. 9C. Lung metastases of MDA-MB-231 cells expressing control (CON) or TMEPAI shRNA. FIG. 9D. Histological sections of lungs from mice injected with MDA-MB-231 cells expressing control (CON) or TMEPAI shRNA.

FIG. 10A. Celastrol inhibited growth and induced death in MDA-MB-231 breast cancer cells even at 1 micromolar concentration. FIG. 10B. Celastrol had no effect on the growth of normal mammary epithelial cells MCF-10A. FIG. 10C. Celastrol inhibited non-Smad signaling (left panel) and enhanced Smad signaling (right panel) by inhibiting TMEPAI expression. FIG. 10D. Celastrol enhanced Smad signaling as measured by 12XCAGA-Luciferase reporter assay.

FIG. 11A. athymic mice bearing subcutaneous MDA-MB-231 tumors that were treated for 3 times a week for 4 consecutive weeks with 2 mg/kg celastrol or vehicle alone. FIG. 11B. Tumor weights following celastrol treatment, P<0.001. Inset shows relative sizes of tumors isolated from vehicle and celastrol treated mice. FIG. 11C. Celastrol treated tumors exhibit increased TGF-β signaling through formation of pSmad2 and pSmad3 and decreased TMEPAI expression FIG. 11D. Toxicity of celastrol administered was monitored by measuring total body weight.

(FIG. 12A) Representative pictures of tumors excised from nude mice that harbored xenografts of human breast cancer cells (MDA-MB-231). (Veh-NP) 2 mg/kg drug-free liposomes, 0.2 mg/kg celastrol containing liposomes (CLST-NP) or 2 mg/Kg celastrol alone (CLST) were administered by intraperitoneal injection every alternate day for first week and every 2 day interval for following week for a total of two weeks period. (FIG. 12B) Tumor weights were shown *p<0.01 versus Vehicle control group. (FIG. 12C) Tumor volumes measured before sacrificing the animals. * p<0.01 versus Vehicle control group. (FIG. 12D) Similarities in body weights of animals treated with vehicle or drugs indicate non-toxicity of CLST-NP and CLST at the doses administered.

(FIG. 13A) Representative pictures of Western blots for TMEPAI protein in exosomes isolated from the culture medium devoid of cells after cells were grown for 24 and 48 h with or without TGF-β. (FIG. 13B) Comparison of proteins, by Western blot, present in exosomes isolated from culture medium after growing wild-type and TMEPAI deficient (TMEPAIKD) MDA-MB-231 cells.

DESCRIPTION OF ILLUSTRATIVE EMBODIMENTS

Figure 1A:
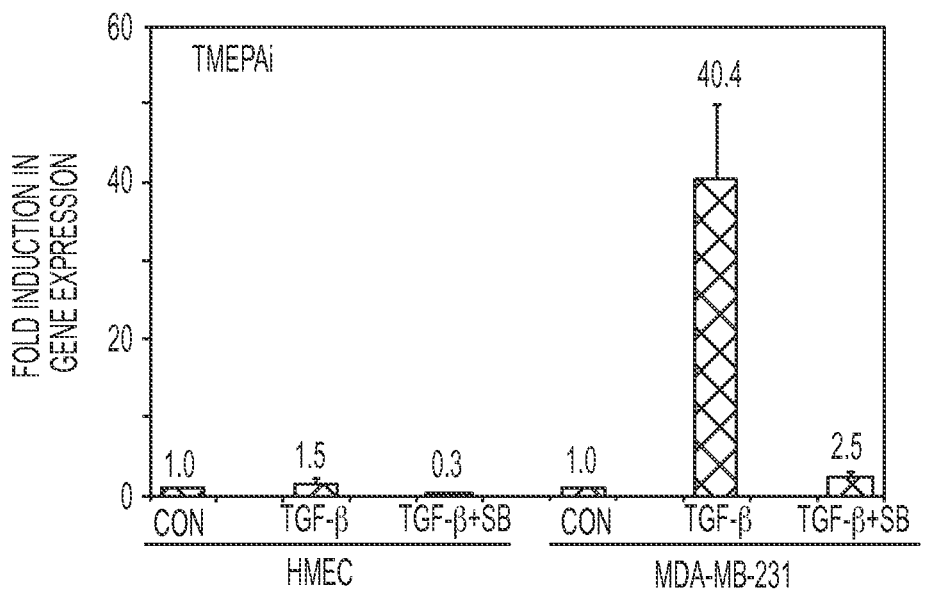
FIGS. 1A-B: Relative expression of TMEPAI mRNA and protein in normal and cancer cells.

TGF-beta has paradoxical functions in tumor progression. Identifying the molecular switch between these two functions could provide new mechanistic insights of how it functions in breast cancer progression and new therapeutic targets. The inventors previously reported that TMEPAI gene expression converts transforming growth factor-beta (TGF-β) from a tumor suppressor to a tumor promoter. TMEPAI acting as a molecular switch between two functions of TGF-β can be used to identify patients that will benefit from the TGF-beta-based anticancer therapy and also serve as surrogate marker to monitor the progress of patients treated with the therapy. Now, the inventors show that TMEPAI promotes breast cancer cell proliferation and migration through stimulation of TGF-β mediated noncanonical signaling pathways while suppressing TGF-β mediated canonical signaling. TMEPAI gene knockdown in triple-negative breast cancer cells reestablishes high Smad signaling (canonical signaling) and suppresses non-canonical signaling thus restoring the homeostatic regulation by TGF-β. The inventors also identified a plant derived triterpinoid having the ability to suppress TMEPAI expression and stimulate canonical Smad signaling. This agent inhibited cell proliferation as well as induced cell death in breast cancer cells. Therefore, chemotherapeutic antagonization of TMEPAI can restore the cytostatic function of TGF-β by restoring the normal balance between TGF-β-mediated canonical and non-canonical signaling pathways. Indeed, preclinical studies confirm that TMEPAI-expressing breast cancers are susceptible to pharmacological inhibition of TMEPAI expression by this terpinoid. To facilitate bioavailability of the drug, a nanoparticle formulation of this agent can be employed.

These and other aspects of the invention are described in greater detail below.

I. TMEPAI

Transmembrane prostate androgen-induced (TMEPAI), alternatively termed PMEPA1, STAG1, ERG1.2, or N4wbp4, has been reported to be induced by testosterone or its derivatives and to be implicated in tumorigenesis. The transcript of TMEPAI has also been shown to be induced by TGF-β. TMEPAI is a type Ib transmembrane protein containing two PY motifs that can interact with HECT-type E3 ubiquitin ligases. TMEPAI has been reported to be involved in p53-mediated apoptosis and cell growth inhibition. However, the mechanisms of its action and physiological function are not fully understood. TMEPAI, a direct target gene of TGF-β signaling, antagonizes TGF-β signaling by interfering with TGF-β type I receptor (TβRI)-induced R-Smad phosphorylation. TMEPAI can directly interact with R-Smads via a Smad interaction motif. TMEPAI competes with Smad anchor for receptor activation for R-Smad binding, thereby sequestering R-Smads from TβRI kinase activation. In mammalian cells, ectopic expression of TMEPAI inhibited TGF-β-dependent regulation of plasminogen activator inhibitor-1, JunB, cyclin-dependent kinase inhibitors, and c-myc expression, whereas specific knockdown of TMEPAI expression prolonged duration of TGF-β-induced Smad2 and Smad3 phosphorylation and concomitantly potentiated cellular responsiveness to TGF-β. Consistently, TMEPAI inhibits activin-mediated mesoderm formation in *Xenopus* embryos. Therefore, TMEPAI participates in a negative feedback loop to control the duration and intensity of TGF-β/Smad signaling. TMEPAI has also been shown to interact with NEDD4.

II. CANCERS

Cancer results from the outgrowth of a clonal population of cells from tissue. The development of cancer, referred to as carcinogenesis, can be modeled and characterized in a number of ways. An association between the development of cancer and inflammation has long been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Cancer cells to which the methods of the present invention can be applied include generally any cell that expresses, and more particularly, that overexpresses TMEPAI. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present invention may be particularly applied to such cancers so as to render them resectable, to prolong or re-induce remission, to prevent or limit metastasis, and/or to treat multi-drug resistant cancers.

III. INHIBITORS

A. Antibodies

1. General Methods

It will be understood that monoclonal antibodies binding to TMEPAI will have utilities in several applications. These include the production of diagnostic kits for use in detecting and diagnosing cancer. In these contexts, one may link such antibodies to diagnostic or therapeutic agents, use them as capture agents or competitors in competitive assays, or use them individually without additional agents being attached thereto. The antibodies may be mutated or modified, as discussed further below. Also, the antibodies are useful as therapeutic agents, as described elsewhere in this document. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this invention were generated using the SP2/0/mIL-6 cell line, an IL-6 secreting derivative of the SP2/0 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vivo, where the MAbs are naturally secreted into the culture medium from which they can be readily obtained in high concentrations. Alternatively, human hybridoma cells lines can be used in vivo to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

2. Engineering of Antibody Sequences

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells). The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR products can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into a Lonza pConIgG1 or pConK2 plasmid vector, transfected into 293 Freestyle cells or Lonza CHO cells, and antibodies were collected an purified from the CHO cell supernatant. The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vivo or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 20 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution.

Jones et al. (1986); Verhoeyen et al. (1988); Beidler et al. (1988); all of which are incorporated herein by reference. In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention also contemplates isotype modification. By modifying the Fc region to have a different isotype, different functionalities can be achieved. For example, changing to IgG4 can reduce immune effector functions associated with other isotypes. Modified antibodies may be made by any technique known to those of skill in the art, including expression through standard molecular biological techniques, or the chemical synthesis of polypeptides. Methods for recombinant expression are addressed elsewhere in this document.

3. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide.

Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C-terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, heterobifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibodyconjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

4. Intrabody

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997). By virtue of their ability to enter cells, intrabodies have additional uses that other types of antibodies may not achieve. In the case of the present antibodies, the ability to interact with DC-HIL on the surface of mdsc's may interfere with functions associated with DC-HIL, such as signaling functions (binding to other molecules) or oligomer formation. In particular, it is contemplated that such antibodies can be used to inhibit DC-HIL interaction with T cells. While the target for these antibodies is intracellular by nature, recent reports suggest that the large size of even fully intact antibodies is not necessarily an impediment to their efficacy.

Guo et al. (2011) report that overexpressed internal tumor antigens, including those that are artificial and non-transforming (eGFP), can be targeted by intact antibodies which in turn can exhibit anti-tumor activity (inhibition of metastasis, inhibition of tumor progression, increased patient survival, reduced tumor load). Thus, while the use of intrabodies or antibody conjugates may prove useful, the modifications do not appear to be required for treatment efficacy.

5. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques. In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.). Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

B. Nucleic Acid Inhibitors

In certain embodiments, the USPS inhibitor is a double-stranded RNA (dsRNA) directed to an mRNA for USPS. In such embodiments, the dsRNA mediates the reduction of the expression of USPS, which leads to reduced de-ubiquitination.

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). It is generally accepted that RNAi acts post-transcriptionally, targeting RNA transcripts for degradation. It appears that both nuclear and cytoplasmic RNA can be targeted (Bosher and Labouesse, 2000).

1. siRNA siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). siRNA are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

2. shRNA

Short hairpin RNA (shRNA) is a sequence of RNA that makes a tight hairpin turn that can be used to silence gene expression. shRNA is transcribed by RNA polymerase III. shRNA production in a mammalian cell can sometimes cause the cell to mount an interferon response as the cell seeks to defend itself from what it perceives as viral attack. Paddison et al. (2002) examined the importance of stem and loop length, sequence specificity, and presence of overhangs in determining shRNA activity. The authors found some interesting results. For example, they showed that the length of the stem and loop of functional shRNAs could vary. Stem lengths could range anywhere from 25 to 29 nt and loop size could range between 4 to 23 nt without affecting silencing activity. Presence of G-U mismatches between the 2 strands of the shRNA stem did not lead to a decrease in potency. Complementarity between the portion of the stem that binds to the target mRNA (antisense strand) and the mRNA, on the other hand, was shown to be critical. Single base mismatches between the antisense strand of the stem and the mRNA abolished silencing. It has been reported that presence of 2 nt 3'-overhangs is critical for siRNA activity (Elbashir et al., 2001). Presence of overhangs on shRNAs, however, did not seem to be important. Some of the functional shRNAs that were either chemically synthesized or in vivo transcribed, for example, did not have predicted 3' overhangs.

3. Production of Inhibitory Nucleic Acids dsRNA can be synthesized using well-described methods (Fire et al., 1998). Briefly, sense and antisense RNA are synthesized from DNA templates using T7 polymerase (MEGAscript, Ambion). After the synthesis is complete, the DNA template is digested with DNaseI and RNA purified by phenol/chloroform extraction and isopropanol precipitation. RNA size, purity and integrity are assayed on denaturing agarose gels. Sense and antisense RNA are diluted in potassium citrate buffer and annealed at 80° C. for 3 min to form dsRNA. As with the construction of DNA template libraries, a procedure may be used to aid this time intensive procedure. The sum of the individual dsRNA species is designated as a "dsRNA library."

The making of siRNAs has been mainly through direct chemical synthesis; through processing of longer, double-stranded RNAs through exposure to *Drosophila* embryo lysates; or through an in vivo system derived from S2 cells. Use of cell lysates or in vivo processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vivo transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vivo or in vivo, using manual and/or automated procedures. This reference also provides that in vivo synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

Several groups have developed expression vectors that continually express siRN. As in stably transfected mammalian cells (Brummelkamp et al., 2002; Lee et al., 2002; Miyagishi and Taira, 2002; Paddison et al., 2002; Paul et al., 2002; Sui et al., 2002; Yu et al., 2002). Some of these plasmids are engineered to express shRNAs lacking (A) tails (Brummelkamp et al., 2002; Paddison et al., 2002; Paul et al., 2002; Yu et al., 2002). Transcription of shRNAs is initiated at a polymerase III (pol III) promoter and is believed to be terminated at position 2 of a 4-5-thymine transcription termination site. shRNAs are thought to fold into a stem-loop structure with 3' UU-overhangs, Subsequently, the ends of these shRNAs are processed, converting the shRNAs into ~21 nt siRNA-like molecules (Brummelkamp et al., 2002). The siRNA-like molecules can, in turn, bring about gene-specific silencing in the transfected mammalian cells.

More generally, most any oligo- or polynucleotide may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vivo chemically synthesis using phosphotriester, phosphite or phosphoramidite chemistry an d solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141, 813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

4. Nucleobases, Nucleosides, Nucleotides and Nucleic Analogs

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moeity. Preferred alkyl (e.g., alkyl, carboxyalkyl, etc.) moeities comprise of from about 1, about 2, about 3, about 4, about 5, to about 6 carbon atoms. A nucleobase may be comprised in a nucleoside or nucleotide, using any chemical or natural synthesis method described herein or known to one of ordinary skill in the art.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety"

generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate Rnase H; and U.S. Pat. No. 5,708,154 which describes RNA linked to a DNA to form a DNA-RNA hybrid.

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

A locked nucleic acid (LNA), often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006). LNA bases may be included in a DNA backbone, by they can also be in a backbone of LNA, 2'-O-methyl RNA, 2'-methoxyethyl RNA, or 2'-fluoro RNA. These molecules may utilize either a phosphodiester or phosphorothioate backbone.

Other oligonucleotide modifications can be made to produce oligomers of the present invention. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A motif having entirely of 2'-O-methyl and 2'-fluoro nucleotides has shown enhanced plasma stability and increased in vivo potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane (BH3-) moiety. Boranophosphate siRNAs (BNAs) have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, NAAs conjugated with cholesterol improve in vivo and in vivo cell permeation in liver cells (Rand et al., 2005). Soutschek et al.

(2004) have reported on the use of chemically-stabilized and cholesterol-conjugated siRNAs have markedly improved pharmacological properties in vivo and in vivo. Chemically-stabilized siRNAs with partial phosphorothioate backbone and 2'-O-methyl sugar modifications on the sense and anti-sense strands (discussed above) showed significantly enhanced resistance towards degradation by exo- and endo-nucleases in serum and in tissue homogenates, and the conjugation of cholesterol to the 3' end of the sense strand of an oligonucleotides by means of a pyrrolidine linker does not result in a significant loss of gene-silencing activity in cell culture. These study demonstrates that cholesterol conjugation significantly improves in vivo pharmacological properties of oligonucleotides.

U.S. Patent Publication No. 2008/0015162, provide additional examples of nucleic acid analogs useful in the present invention. The following excerpts are derived from that document and are exemplary in nature only. In certain embodiments, oligomeric compounds comprise one or more modified monomers, including 2'-modified sugars, such as BNA's and monomers (e.g., nucleosides and nucleotides) with 2'-substituents such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl.

In certain embodiments, the oligomeric compounds including, but no limited to short antisense compounds of the present invention, comprise one or more high affinity monomers provided that the oligomeric compound does not comprise a nucleotide comprising a 2'-O($CH_2$)$_n$H, wherein n is one to six. In certain embodiments, the oligomeric compounds including, but no limited to short antisense compounds of the present invention, comprise one or more high affinity monomer provided that the oligomeric compound does not comprise a nucleotide comprising a 2'-$OCH_3$ or a 2'-O($CH_2$)$_2OCH_3$. In certain embodiments, the oligomeric compounds including, but no limited to short antisense compounds of the present invention, comprise one or more high affinity monomer provided that the oligomeric compound does not comprise a α-L-methyleneoxy (4'-$CH_2$—O-2') BNA. In certain embodiments, the oligomeric compounds comprise one or more high affinity monomer provided that the oligomeric compound does not comprise a β-D-methyleneoxy (4'-$CH_2$—O-2') BNA and/or a β-D-methyleneoxy (4'-$CH_2$—O-2') BNA.

Certain BNA's have been prepared and disclosed in the patent literature as well as in scientific literature (Singh et al., 1998; Koshkin et al., 1998; Wahlestedt et al., 2000; Kumar et al., 1998; WO 94/14226; WO 2005/021570; Singh et al., 1998). Examples of issued US patents and published applications that disclose BNA's include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-$CH_2$—O-2') linkage to form the bicyclic sugar moiety (reviewed in Elayadi et al., 2001; Braasch et al., 2001, and Orum et al., 2001; see also U.S. Pat. Nos. 6,268,490 and 6,670,461). The linkage can be a methylene (—$CH_2$—) group bridging the 2' oxygen atom and the 4' carbon atom, for which the term methyleneoxy (4'-$CH_2$—O-2') BNA is used for the bicyclic moiety; in the case of an ethylene group in this position, the term ethyleneoxy (4'-$CH_2CH_2$—O-2') BNA is used (Singh et al., 1998; Morita et al., 2002). Methyleneoxy (4'-$CH_2$—O-2') BNA and other bicyclic sugar analogs display very high duplex thermal stabilities with complementary DNA and RNA ($T_m$=+3 to +10° C.), stability towards 3'-exonucleolytic degradation and good solubility properties. Potent and nontoxic antisense oligonucleotides comprising BNAs have been described (Wahlestedt et al., 2000).

An isomer of methyleneoxy (4'-$CH_2$—O-2') BNA that has also been discussed is α-L-methyleneoxy (4'-$CH_2$—O-2') BNA which has been shown to have superior stability against a 3'-exonuclease. The α-L-methyleneoxy (4'-$CH_2$—O-2') BNA's were incorporated into antisense gapmers and chimeras that showed potent antisense activity (Frieden et al., 2003).

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., 1998). BNAs and preparation thereof are also described in WO 98/39352 and WO 99/14226.

Analogs of methyleneoxy (4'-$CH_2$—O-2') BNA, phosphorothioate-methyleneoxy (4'-$CH_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

Modified sugar moieties are well known and can be used to alter, typically increase, the affinity of oligomers for its target and/or increase nuclease resistance. A representative list of modified sugars includes, but is not limited to, bicyclic modified sugars (BNA's), including methyleneoxy (4'-$CH_2$—O-2') BNA and ethyleneoxy (4'-($CH_2$)$_2$—O-2' bridge) BNA; substituted sugars, especially 2'-substituted sugars having a 2'-F, 2'-$OCH_3$ or a 2'-O($CH_2$)$_2$—$OCH_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

The naturally-occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleotide backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

5. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vivo reaction components such as for example, macromolecules such as lipids or proteins, small biological molecules, and the like.

C. Small Molecules

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). An ongoing effort for the improvement of anti-inflammatory and antiproliferative activity of oleanolic and ursolic acid analogs led to the discovery of 2-cyano-3,12-dioxooleane-1,9(11)-dien-28-oic acid (CDDO) and related compounds (Honda et al., 1997, 1998, 1999, 2000a, 2000b, 2002; Suh et al., 1998; 1999; 2003; Place et al., 2003; Liby et al., 2005). Several potent derivatives of oleanolic acid were identified, including methyl-2-cyano-3,12-dioxooleana-1,9-dien-28-oic acid (CDDO-Me). CDDO-Me suppresses the induction of several important inflammatory mediators, such as iNOS, COX-2, TNFα, and IFNγ, in activated macrophages. CDDO-Me has also been reported to activate the Keap1/Nrf2/ARE signaling pathway resulting in the production of several anti-inflammatory and antioxidant proteins, such as heme oxygenase-1 (HO-1). These properties make CDDO-Me, as well as other triterpenoids, candidates for the treatment of neoplastic and proliferative diseases, such as cancer.

IV. PHARMACEUTICAL FORMULATIONS AND ROUTES OF ADMINISTRATION

A. Pharmaceutical Formulations

Where clinical applications in treating pain are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, intrathecal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

One particular formulation for delivery is a nanoparticle. Nanoparticles (NPs) are particles ranging in size from 1 to 100 nm. Liposomes are lipid bilayers as closed spherical vesicles that can encapsulate drugs. The general diameter of the liposomes varies from 400 nm to 2.5 mm. These two unique physical and chemical properties can be exploited for drug delivery through drug conjugation and production of solid lipid nanoparticles (SLNP). SLNP are composed of solid lipid dispersed in an aqueous medium and is stabilized by a surfactant. The mean particle size of SLNP is in range of about 40 to 1000 nm. Through high pressure mixing and filtration 40-100 nm size nanoparticles can be obtained. The lack of biodegradability of many nanomaterials, like Fullerenes and carbon nanotubes that were considered to be used as hollow spheres and tubes respectively for transportation of drugs to their target sites, is an important factor for their toxicity. The main advantage of lipid nanoparticles is that they are easily and completely biodegradable because lipids are natural components of all organisms.

B. Subjects

The methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Measurement of TMEPAI as a Biomarker

The results here indicate that elevated expression of TMEPAI carries an unfavorable prognostic significance in cancer patients, including triple-negative breast cancers. Inhibition of TMEPAI expression prevented metastasis and inhibited tumor growth in vivo. Thus, measurement of TMEPAI provides a valuable biomarker to identify patients for whom inhibition of TMEPAI expression would be beneficial. Since gene amplification and/or epigenetic changes at the promoter may underlie increased expression of TME- PAI, it is imperative to analyze the gene dosage and expression of TMEPAI in tumor samples.

Deregulated cellular signaling through altered gene function by epigenetic modifications, point mutations, translocations, amplifications or deletions leads to the cancer phenotype. Upon transformation of normal cells into cancer cells, their progression into overt cancers is blocked by transforming growth factor-β through causing growth arrest or death. Thus, TGF-β represents an important barrier against tumor development in vivo along with immune surveillance. Although, TGF-β is tumor suppressive and inhibits epithelial proliferation, however in some cancers, tumor suppression by TGF-β is subverted to tumor promotion and thus making cancers TGF-β dependent and clinically aggressive. TGF-β antagonism in these cancers may serve as potential treatment option. However, such interventions may adversely affect normal tissues that depend on TGF-β for homeostasis. A better approach is to identify signaling abnormalities downstream of TGF-β and develop strategies to specifically correct their dysfunction while preserving TGF-β tumor suppressive effects. Earlier, the inventors showed that a high frequency of amplification of Transmembrane Prostate Androgen-Induced (TMEPAI) gene locus mapped to 20q13 in ductal carcinoma in situ (DCIS) by array comparative genomic hybridization and high expression of TMEPAI in several invasive breast cancer cell lines. TMEPAI is amplified in high grade breast cancers, and induced to even higher levels by TGF-β in aggressive breast cancer cells. TMEPAI knockdown decreased basal and TGF-β-induced proliferation and migration of cancer cells in vivo and tumor growth in vivo. Furthermore, in normal human mammary epithelial cells (HMEC), TGF-β induced TMEPAI only marginally and inhibited their growth. Thus, TMEPAI, which acts as a molecular switch between two functions of TGF-β, could potentially be used as a novel biomarker to triage patients that will benefit from the TGF-beta-based anticancer therapy and could also serve as surrogate marker to monitor the progress of patients treated with the therapy.

Various methods may be employed to measure TMEPAI as a biomarker:
  TMEPAI mRNA may be measured by quantitative RT-PCR and the protein by immunoblotting on frozen tumor samples.
  For in situ measurements, sections of frozen or paraffin embedded samples may be used for in situ hybridization (ISH) to detect mRNA or immunohistochemistry (IHC) to detect protein.
  The inventors have identified a TMEPAI antibody suitable for IHC and oligonucleotide probes for mRNA. Samples may be scored by, binary (negative and positive) scoring method and/or H-Score method=(percent cells (0-100%)×intensity (0-no stain, 1-weak stain, 2-moderate stain, 3-strong stain).
  To determine TMEPAI gene amplification in tumors, fluorescent in situ hybridization (FISH) may be used on paraffin embedded samples. The probe mixture will contain spectrum orange-labeled TMEPAI probe on chromosome 20q13.31 and a spectrum green labeled centromere probe (D20Z1) for chromosome 20. This test will allow simultaneous detection of both TMEPAI copy number and ploidy. Since the normal copy number of both these gene probes is 2, the normal results will be of 2 green signals and 2 red orange signals. Any variations from the expected ratio indicate either amplification or multiple copies.
  To determine the presence of TMEPAI protein in the serum, possibly secreted into the blood by the tumors that are expressing TMEPAI protein.

V. COMBINATION THERAPIES

One goal of current cancer research is to find ways to improve efficacy, reduce side effects and prevent the development of resistance. One way is by combining such traditional therapies with the therapies of the present invention. In the context of the present invention, it is contemplated that an anti-TMEPAI therapy could be used similarly in conjunction with more standard cancer treatments.

The therapies would be provided in a combined amount effective to reduce pain in a subject, to reduce side effects associated with one or the other agent alone, or to avoid patient tolerance or addiction. This process may involve contacting the patient with the agents/therapies at the same time. This may be achieved by contacting the patient with a single composition or pharmacological formulation that includes both agents, or by contacting the cell with two distinct compositions or formulations, at the same time, wherein one composition includes the USPS therapeutic and the other includes the agent.

Alternatively, the treatment according to the present invention may precede or follow the other treatment by intervals ranging from minutes to weeks. In embodiments where the standard treatment and the anti-TMEPAI treatment are applied separately to the cell, one would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the anti-TMEPAI treatment or the other therapy will be desired. Various combinations may be employed, where the TMEPAI therapy is "A," and the other therapy is "B," as exemplified below:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated, including chronic dosing of one or both agents.

Agents or factors suitable for use in a combined therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site; alternatively, the tumor cells may be contacted with the agent by administering to the subject a therapeutically effective amount of a pharmaceutical composition.

Various classes of chemotherapeutic agents are comtemplated for use with in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with an anti-TMEPAI therapy, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining TMEPAI therapies with chemo- and radiotherapies, it also is contemplated that combination with immunotherapy, hormone therapy, toxin therapy and surgery.

V. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Preparation of CLST-NP. Nanoparticles were prepared from lecithin emulsions. To prepare vehicle (Veh-NP) and celastrol (CLST-NP)-loaded nanoparticles, 10 mg of celastrol in ethanol was added into a glass vial containing 4 mg of lecithin and evaporated the ethanol completely using nitrogen gas. Tween 20 in deionized water was added drop wise method to a final concentration of 2% (w/v) and heat it in magnetic stirrer hot plate at 50-55° C. with small magnetic flee till milky dispersion, less opaque but not clear solution formed. Same procedure was repeated without drug to make vehicle loaded lecithin nanoparticle (Veh-NP or Veh). Both Veh-NP and CTR-NP were filtered through series of 0.4μ, 0.2μ, 0.1μ membranes and added 5% dextrose as lyoprotectant. Freeze dried the total volume of both Veh-NP and CLST-NP and dissolved in deionized water. Quantification of nanoparticle was done at 425 nm. The nanoparticle was observed under scanning electron microscopy (SEM) and particle size was measured by dynamic light scattering (DLS).

Example 2

Results

TMEPAI Expression in Normal Mammary Epithelial Cells Vs Breast Cancer Cells. Transmembrane Prostate Androgen-Induced (TMEPAI) mRNA (>40-fold) and proteins (~9-fold) were greatly induced in MDA-MB-231 cells that are exposed to the tumor suppressive cytokine TGF-β

Figure 1B:
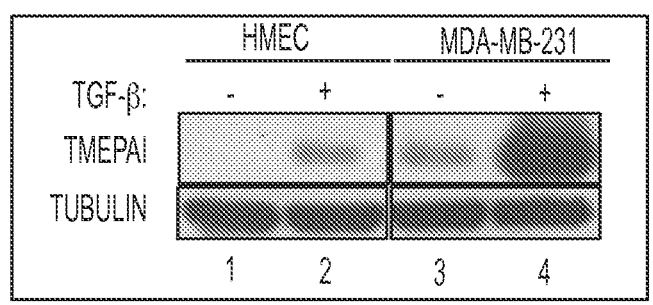
Figure 2:
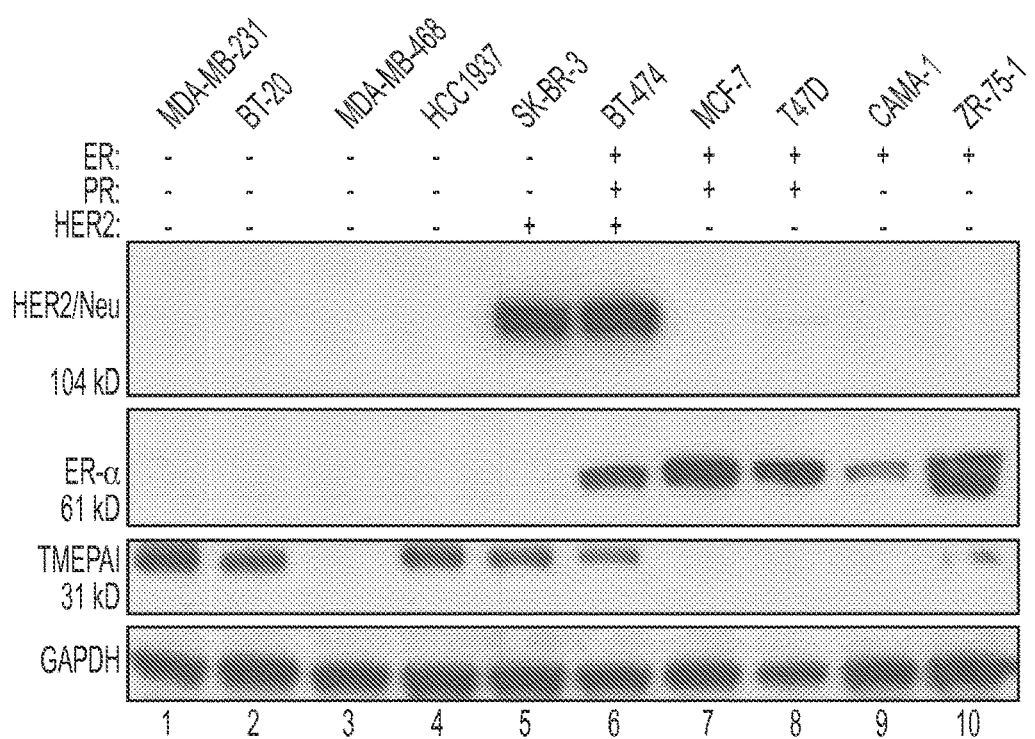
FIG. 2: Relative Expression of TMEPAI, ER-α and HER2 proteins in various breast cancer cells. Western blot analysis for TMEPAI, estrogen receptor-alpha (ER), progesterone receptor (PR) and Her2 receptor (Her2) in invasive and non-invasive breast cancer cell lines

(FIGS. 1A-B) within 6 h of treatment. In contrast, normal human mammary epithelial cells (HMEC) poorly induced TMEPAI RNA and proteins (FIGS. 1A-B) in response to TGF-β. The inventors tested the expression of TMEPAI in various breast cancer lines by immunoblotting. While most aggressive triple-negative (MDA-MB-231, BT20, HCC1937) cells expressed TMEPAI protein, the ER +ve but non-invasive, MCF-7, T47D, and CAMA-1 cells did not significantly express this protein (FIG. 2). Moreover, TMEPAI is also expressed by aggressive HER2-positive breast cancer cells that either coexpress estrogen receptor (BT-474) or not (SK-BR-3) (FIG. 2).

Figures 3A, 3B:
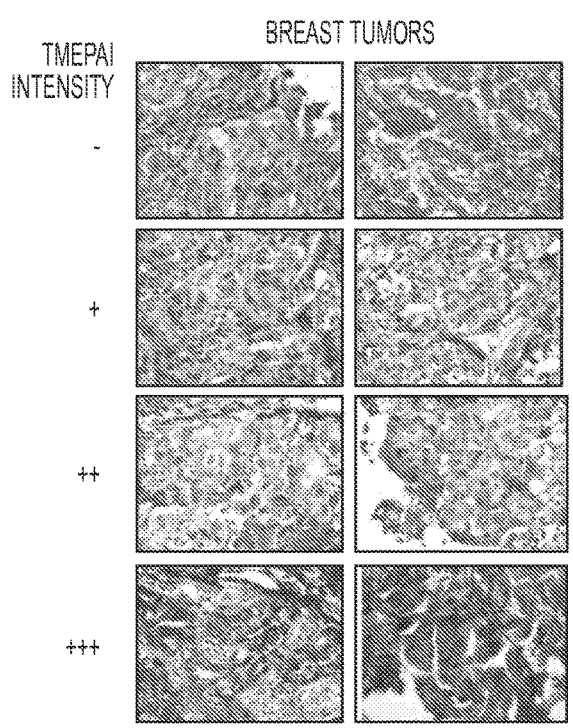
FIG. 3A-B: Immunohistochemistry (IHC) for TMEPAI protein in breast tumors.

TMEPAI Protein Expression in Breast Tumors. Earlier, the inventors demonstrated that a higher frequency of amplification of TMEPAI mapped to 20q13 (1, 2) in ductal carcinoma in situ (DCIS) (43/85) compared to lobular carcinoma in situ LCIS (2/11) by array comparative genomic hybridization (aCGH). They also identified that TMEPAI is highly expressed in several invasive breast cancer cell lines (2). To further explore the possible role of TMEPAI in mammary carcinogenesis, several breast tumors were screened for TMEPAI expression by immunohistochemistry (IHC). To validate the aCGH data of gene amplification to real protein expression, 17 cases of DCIS were randomly selected with 8 of these (47%) cases were showing gene amplification in TMEPAI locus (FIGS. 3A-B). Among these, little or no TMEPAI protein expression was found in 3 cases (18%). In 4 out of 17 (24%), low expression (+) of TMEPAI protein was seen, while 10 of 17 (59%) cases showed moderate to marked (++/+++) expression of TMEPAI protein. In contrast to aCGH, where only 47% (8/17) of cases were positive for TMEPAI gene amplification, IHC identified 82% (14/17) of DCIS cases with elevated TMEPAI protein expression. These results suggest that both genetic and epigenetic events may be involved in elevating TMEPAI expression in ductal neoplasias.

Figure 4A:
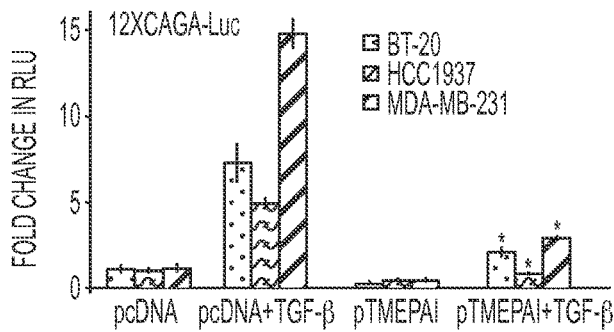
FIGS. 4A-H: TMEPAI downregulates canonical Smad signaling.
Figure 4B:
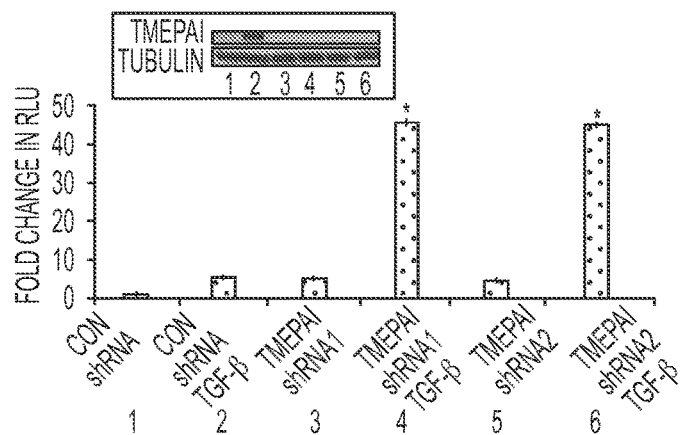
Figure 4C:
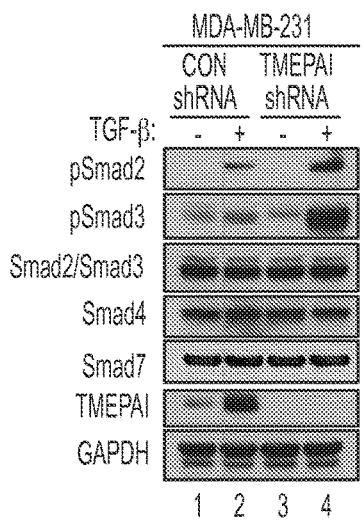
Figure 4D:
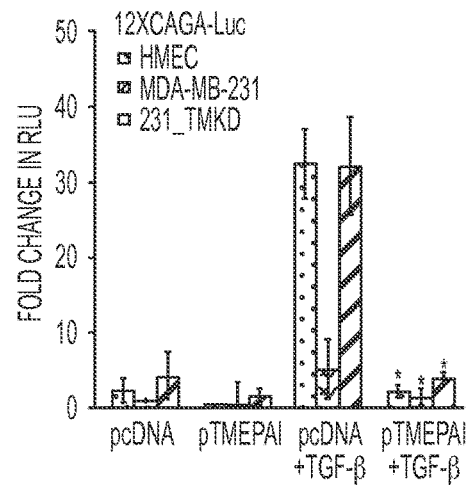
Figure 4E:
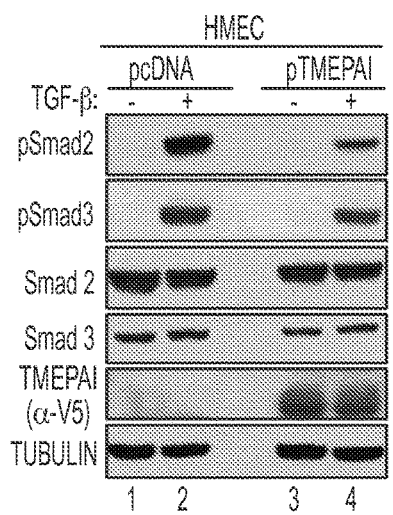
Figure 4F:
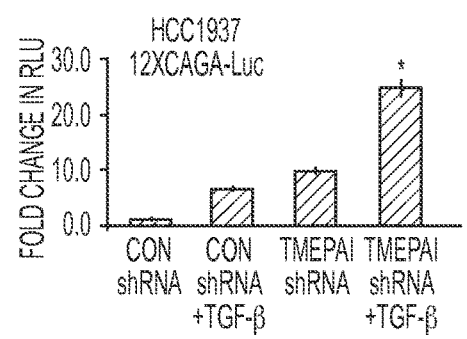
Figure 4G:
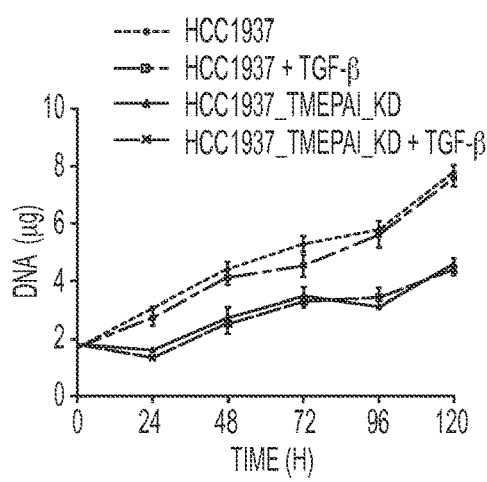
Figure 4H:
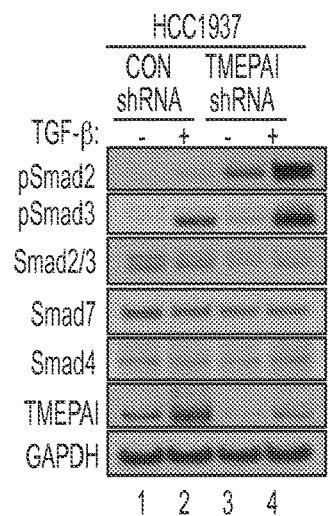
Figure 5A:
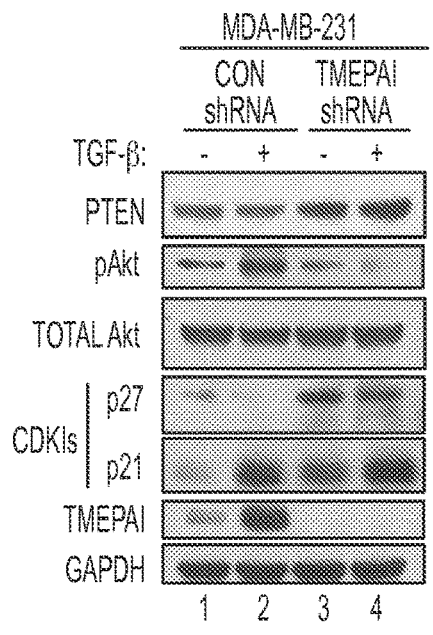
FIGS. 5A-C: TMEPAI upregulates non-canonical signaling in breast cancer cells.
Figure 5B:
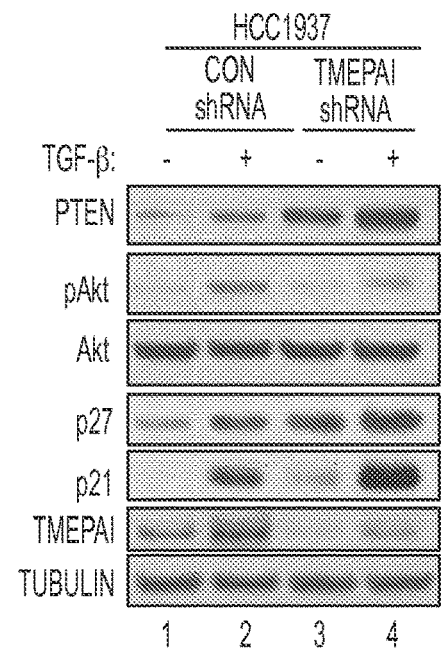
Figure 5C:
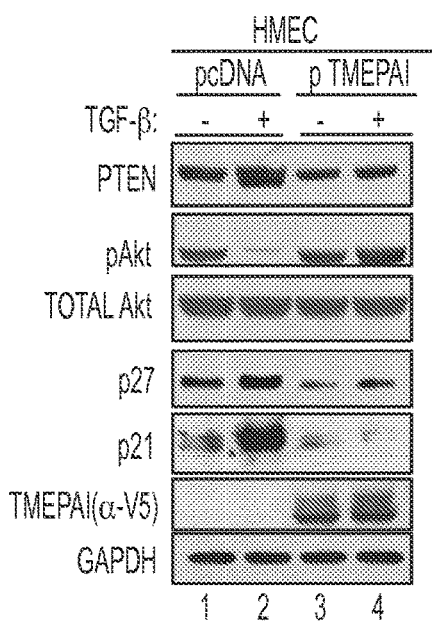

TMEPAI Protein Expression in Breast Tumors Alters TGF-β Signaling. TGF-β signals through Smad-dependent steps and non-canonical pathways involving mitogen activated protein kinases (MAPKs) and phosphatidylinositol 3-kinase (PI3K). Non-canonical signaling can be Smad-independent, but often needs Smad-dependent inputs 1. In this regard, it remained unknown how normally tumor suppressive Smad signaling becomes altered to promote growth and motility of cancer cells with amplified TMEPAI. TMEPAI interacts with Smads2/3 to sequester them from activation by TGF-β receptors (Watanabe et al., 2010), suggesting that TMEPAI promotes tumor growth by decreasing TGF-β growth suppression. However, if this mechanism explains TGF-β mediated growth in cancers, it remained untested. The inventors now identified that tumor promotion by TGF-β in triple-negative cancer cells involves not only TMEPAI dependent abrogation of growth suppressive Smad signaling (FIGS. 4A-H) as predicted by TMEPAI-Smad interactions, but also powerful and unsuspected Smad3 driven TMEPAI activation of non-canonical signaling through PTEN (phosphatase and tensin homolog) and Akt (FIGS. 5A-C). Amplified TMEPAI mediated not only increased proliferation that allows tumor development (FIGS. 8A-D) but also enhanced induction of Snail by TGF-β, favoring metastasis in vivo. (FIGS. 9A-D) The cooperative actions of TMEPAI to decrease growth suppressive Smad signaling together with Smad3-TMEPAI mediated effects on PTEN-Akt to promote growth and metastasis constitute a signaling pathology fundamentally altered from the normal state that may underlie TGF-β tumor promotion in various cancers including triple-negative breast cancers.

Figure 6:
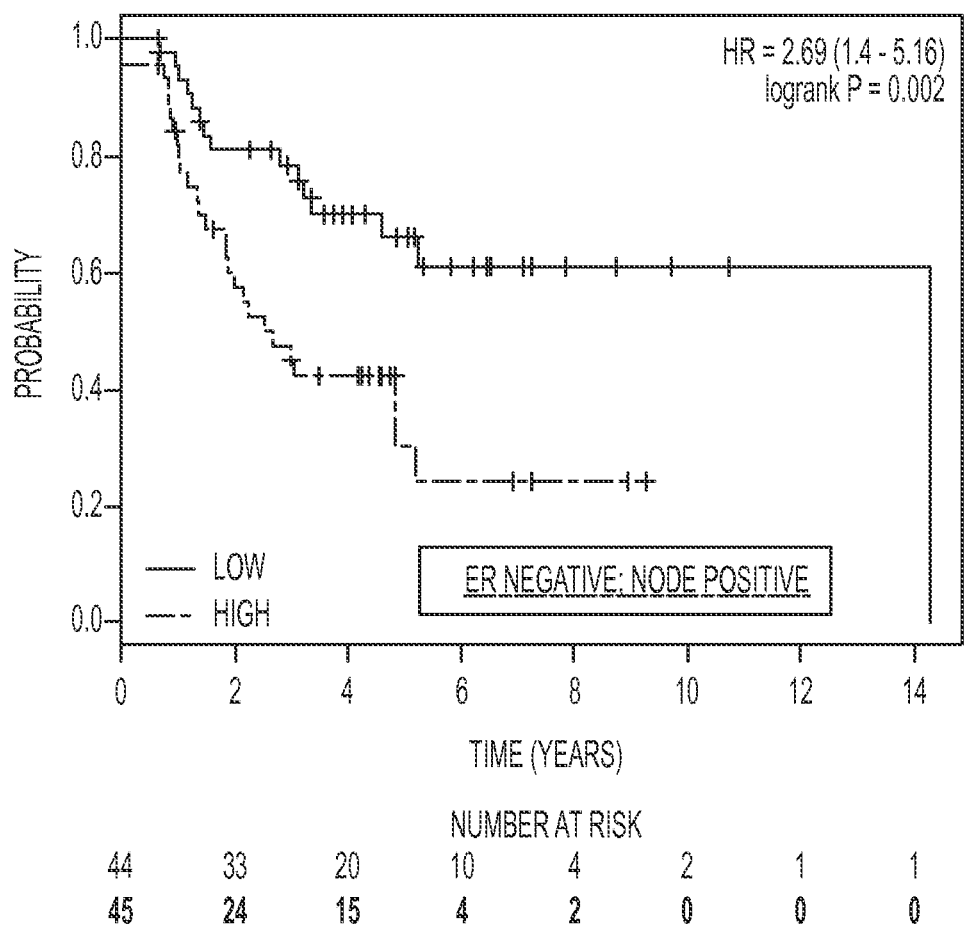
FIG. 6: High TMEPAI expression carries an unfavorable prognostic significance in ER negative/Node positive breast cancer patients. The recurrence-free survival as determined by preliminary analysis of a publicly accessible database with gene expression data and survival information (GEO: Affymetrix HGU133A and HGU133+2 microarrays) of ER/PR negative and lymph node positive patients classified according to TMEPAI expression, at median cut-off, indicated that elevated TMEPAI expression correlates with shorter survival with an hazard ratio (HR) of 2.69 with a log-rank P value of 0.002.
Figure 7A:
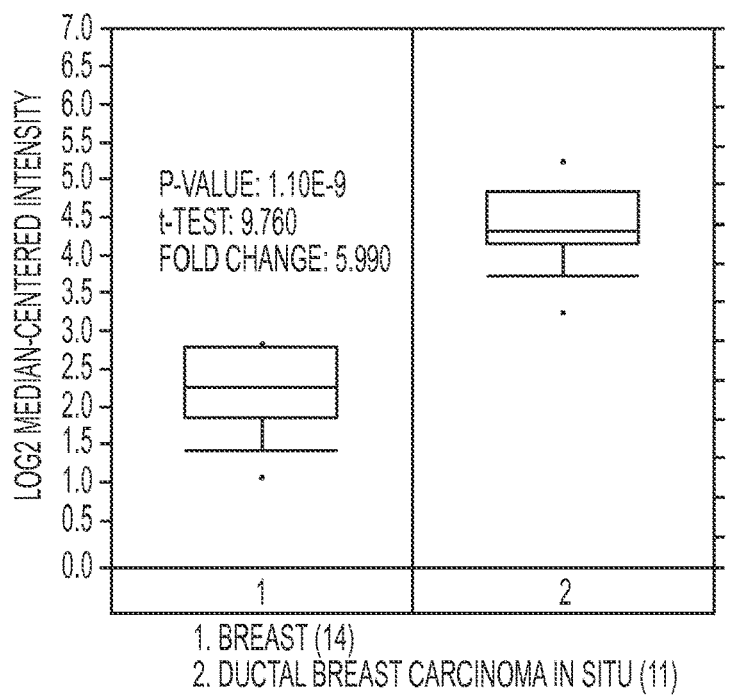
FIGS. 7A-D: Relative mRNA expression of TMEPAI in various cancers by microarray analysis.
Figure 7B:
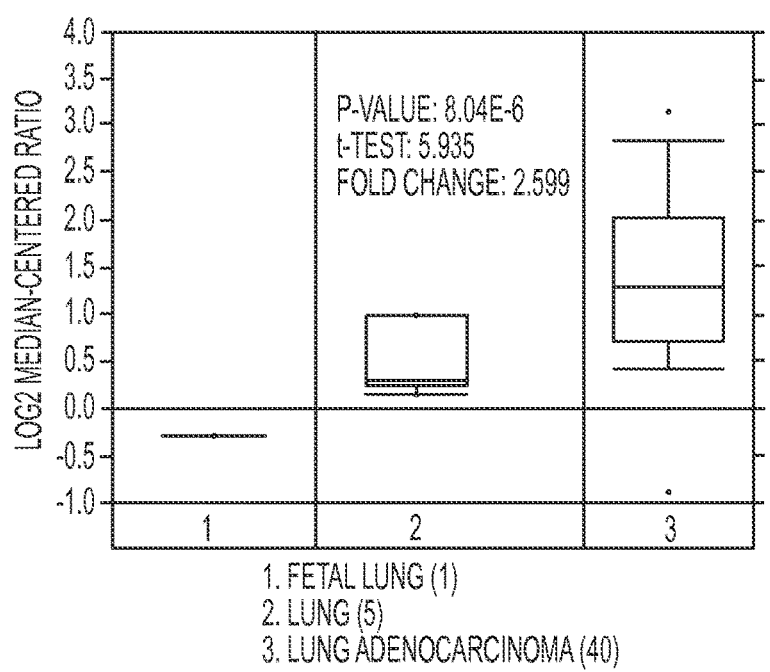
Figure 7C:
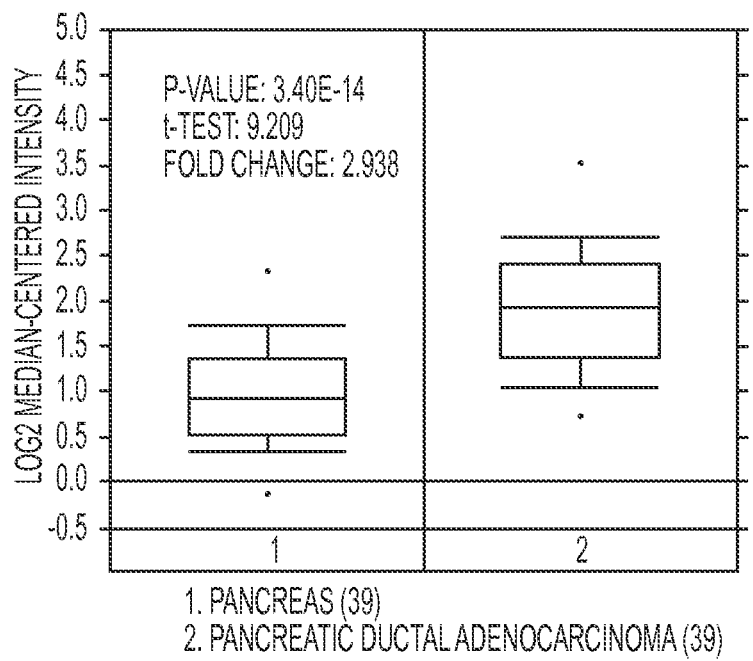
Figure 7D:
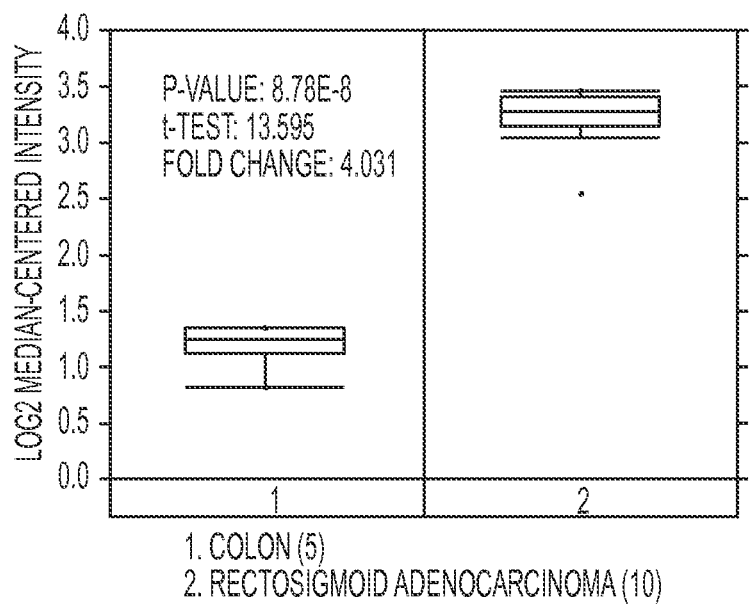

High TMEPAI Expression Carries an Unfavorable Prognostic Significance in ER Negative/Node Positive Breast Cancer Patients. The prognostic significance of TMEPAI was determined by a preliminary analysis was performed on a publicly accessible database and an online tool (Gyorffy, 2010) that was established using gene expression data and survival information downloaded from GEO (Affymetrix HGU133A and HGU133+2 microarrays). The recurrence-free survival of ER negative and lymph node positive patients classified using the median as the reference for TMEPAI expression indicated that high TMEPAI expression correlates with shorter survival with an hazard ratio (HR) of 2.6 with 95% confidence intervals of 1.4-5.16 and a log-rank P value of 0.002 (FIG. 6). Overall, these results indicate that raised expression of TMEPAI mRNA carries an unfavorable prognostic significance in triple-negative breast cancer patients.

Expression of TMEPAI in Normal HMEC Decreases TGF-β Induced Smad Signaling and Inhibition of TMEPAI Expression inMDA-MB-231 Cancer Cells Restores Basally Low Smad Signaling to High Levels. TMEPAI overexpression caused severely reduced Smad signaling, as determined by 12xCAGA driven luciferase (Luc) reporter activity, in MDA-MB-231, BT-20 and HCC1937 cells either in the absence or presence of TGF-β (FIG. 4A). Because TMEPAI can sequester R-Smads and diminish canonical TGF-β signaling, the inventors examined the effects of low TMEPAI in MDA-MB-231 cells and overexpressed TMEPAI in HMEC. TGF-β elicited robust signaling responses in HMEC: C-terminal phosphorylation of Smads2/3 (FIG. 4E) and increased 12xCAGA-Luc activity (FIG. 4D). Expression of TMEPAI in HMEC (that have little basal TMEPAI) suppressed the TGF-β induced phosphorylation of Smads2/3 (FIG. 4E) and decreased 12xCAGA-Luc activity (FIG. 4D). Canonical signaling responses to TGF-β in MDA-MB-231 cells with control shRNA were weak as assessed by C-terminal phosphorylation of Smads2/3 or 12xCAGA-Luc activity (FIGS. 4B, 4C, 4D). On the other hand, TMEPAI knockdown in MDA-MB-231 cells by two different shRNAs restored high 12xCAGA-Luc activity responses to TGF-β (FIGS. 4B and 4D) and increased R-Smad phosphorylation without altering Smads2/3, Smad4 and Smad7 proteins (FIG. 4C). Furthermore, the increased 12XCAGA-Luc activities brought about by TMEPAI knockdown in MDA-MB-231 cells were reduced by expressing mouse-TMEPAI in these cells (FIG. 4D). Thus, MDA-MB-231 cells have defective Smad signaling related to pathologically high TMEPAI and the defect can be corrected by targeting TMEPAI. TMEPAI knockdown in a different triple-negative breast cancer cell line HCC1937, which is refractory to growth suppressive effects of TGF-β (FIG. 4G), resulted in increased Smad3 driven 12XCAGA signaling (FIG. 4F) as well as R-Smad phosphorylation (FIG. 4H) in the presence of TGF-β and reduced growth (FIG. 4G) like MDA-MB-231 cells (Singha et al., 2010; FIGS. 4C and 4D).

Inhibition of TMEPAI Expression in MDA-MB-231 Breast Cancer Cells Blocks and Expression of TMEPAI in Normal HMEC Promotes Non-Canonical TGF-β Signaling Through PTEN and Akt. It is known that TGF-β signaling employs non-canonical effectors such as Aid, a proto-oncogene intermediate in the phosphatidylinositol 3-kinase (PI3K) pathway. The tumor suppressor PTEN antagonizes Akt signaling by dephosphorylating the PI3K product phosphatidylinositol 3,4,5-trisphosphate. The inventors found low levels of PTEN basally and after TGF-β treatment in triple-negative breast cancer cells with control shRNA whereas cells with TMEPAI shRNA had elevated PTEN levels (FIGS. 5A-5B). Correspondingly, Akt phosphorylation was high in response to TGF-β in cancer cells with control shRNA and low PTEN levels, but suppressed in cells with TMEPAI knockdown and greater amounts of PTEN (FIGS. 5A and 5B).

Figure 8A:
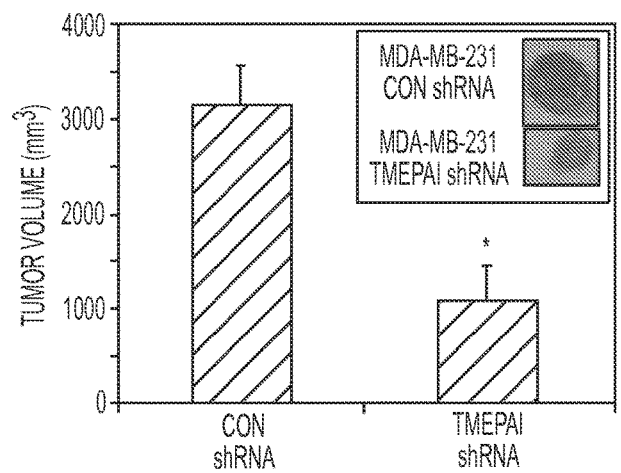
FIGS. 8A-D: Inhibition of TMEPAI expression decreases human breast tumor growth in nude mice.
Figure 8B:
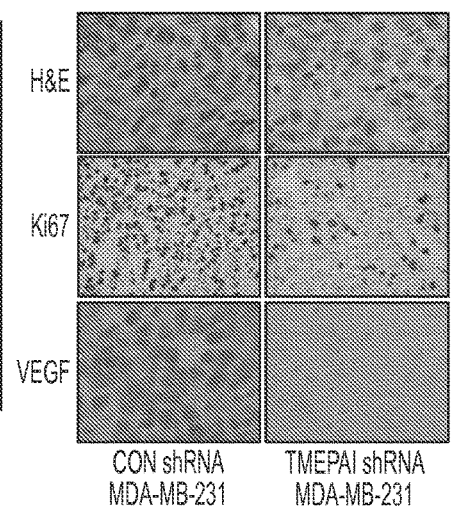
Figure 8C:
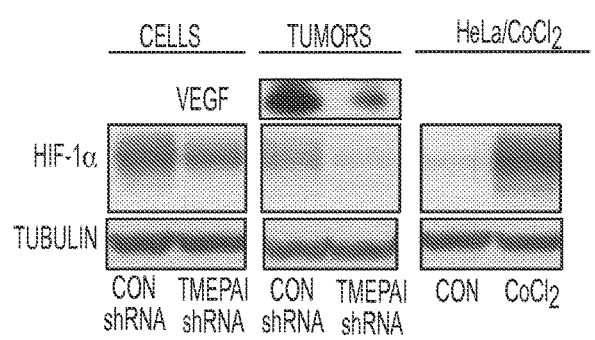
Figure 8D:
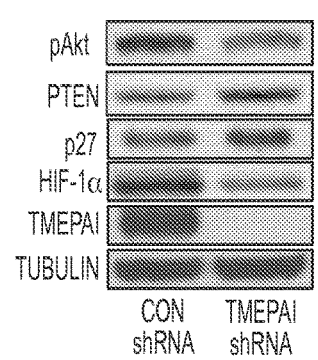
Figure 9A:
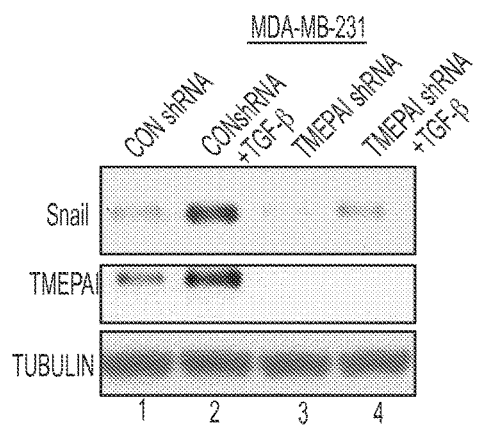
FIGS. 9A-D: Role of TMEPAI and Snail in breast cancer metastasis.
Figure 9C:
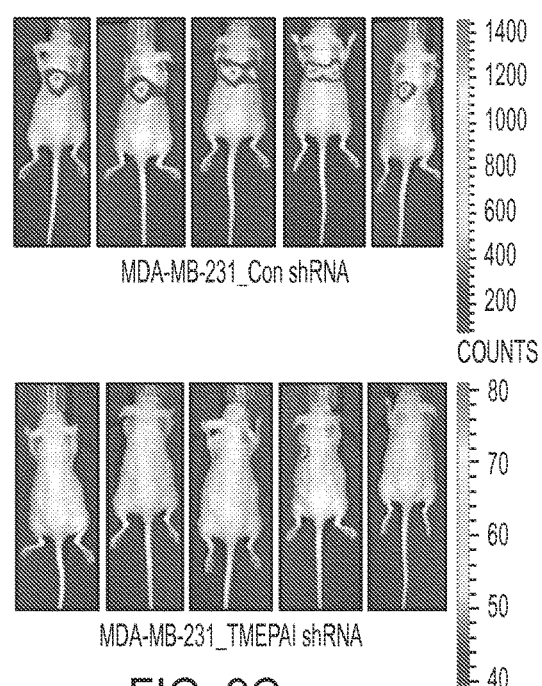
Figure 9B:
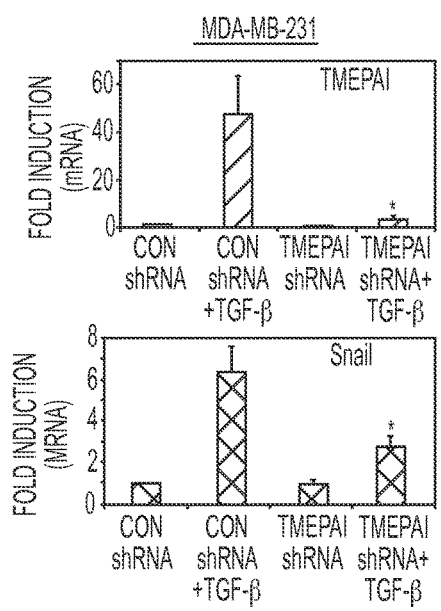
Figure 9D:
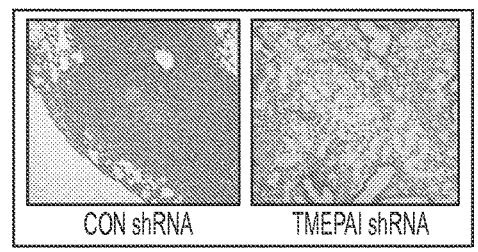

Inhibition of TMEPAI Expression by shRNA Prevented Tumor Metastasis. The inventors showed that TMEPAI knockdown by shRNA in MDA-MB-231 cells markedly decreased the size of tumor xenografts compared to corresponding cells with control shRNA (FIG. 8A), which is consistent with an important role for TMEPAI in TGF-β dependent growth not only in culture (Singha et al., 2010; FIG. 4G), but also in vivo (FIG. 8A). Apart from its role in cell growth and survival, activation of the PI3K/Akt pathway is involved in cancer cell migration and is linked with increased invasiveness of many tumors. These effects of PI3K/Akt are antagonized by the tumor suppressor PTEN that the inventors now show to be a target for TMEPAI. Increased PI3K signaling leads to up-regulation of the transcription factor Snail and reduces cell-cell contacts and promotes epithelial-to-mesenchymal transition. They found that both Snail mRNA and protein were markedly increased by treatment of cells with TGF-β, along with the expected induction of TMEPAI. The effects of TGF-β to increase Snail were blocked by TMEPAI knockdown (FIGS. 9A and 9B). Snail expression can govern tumor invasiveness. Indeed, they showed previously that TMEPAI knockdown decreased MDA-MB-231 cell motility and invasion through extracellular matrices using the Matrigel assay (Singha et al., 2010). In fact, they found that TMEPAI knockdown in MDA-MB-231 cells greatly decreased tumor lung metastases in vivo as well following intravenous injection compared to corresponding cells with control shRNA (FIGS. 9C and 9D).

Figure 10A:
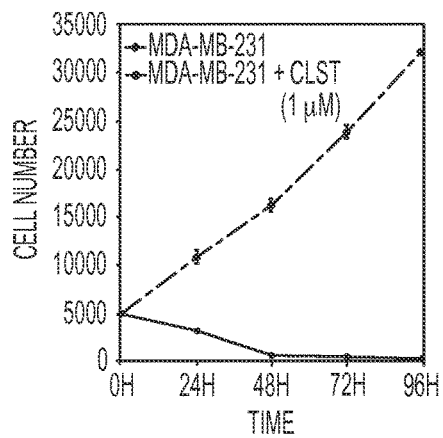
FIGS. 10A-D: Celastrol is novel inhibitor of TMEPAI expression and cancer cell growth by enhancing growth suppressive TGF-β signaling.
Figure 10B:
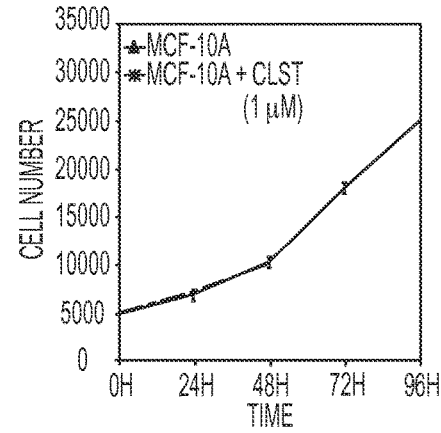
Figure 10C:
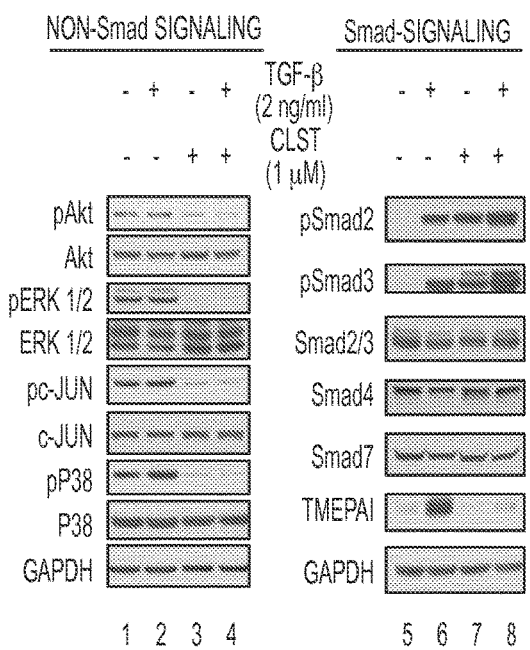
Figure 10D:
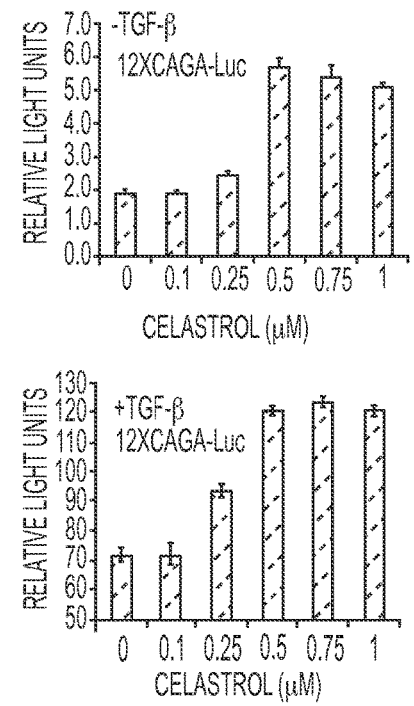

Terpinoid Derivative Celastrol Blocked TMEPAI Expression and Reversed TMEPAI Mediated Effects. The inventors identified tripterine (celastrol), a triterpinoid, having the ability to block TGF-β induced TMEPAI expression after screening several terpinoid derivatives with reactive α,β-unsaturated ketones in their structure. Celastrol at low concentration (1 μM) significantly decreased MDA-MB-231 cancer cell proliferation and increased cell death and had no growth suppressive effect on normal MCF-10A cells (FIGS. 10A and 10B). Only a mild decrease in the proliferation of normal MCF-10A cells was observed even at a 10-fold higher dose of celastrol (not shown). Consistent with its ability to block TMEPAI expression, celastrol significantly increased Smad signaling as measured by Smad2 and Smad3 phosphorylation (FIG. 10C, right panel). Equally, celastrol inhibited non-Smad signaling (FIG. 10C, left panel). The enhancement of Smad signaling is also confirmed by increased 12XCAGA-luciferase reporter activity (FIG. 10D).

Figure 11A:
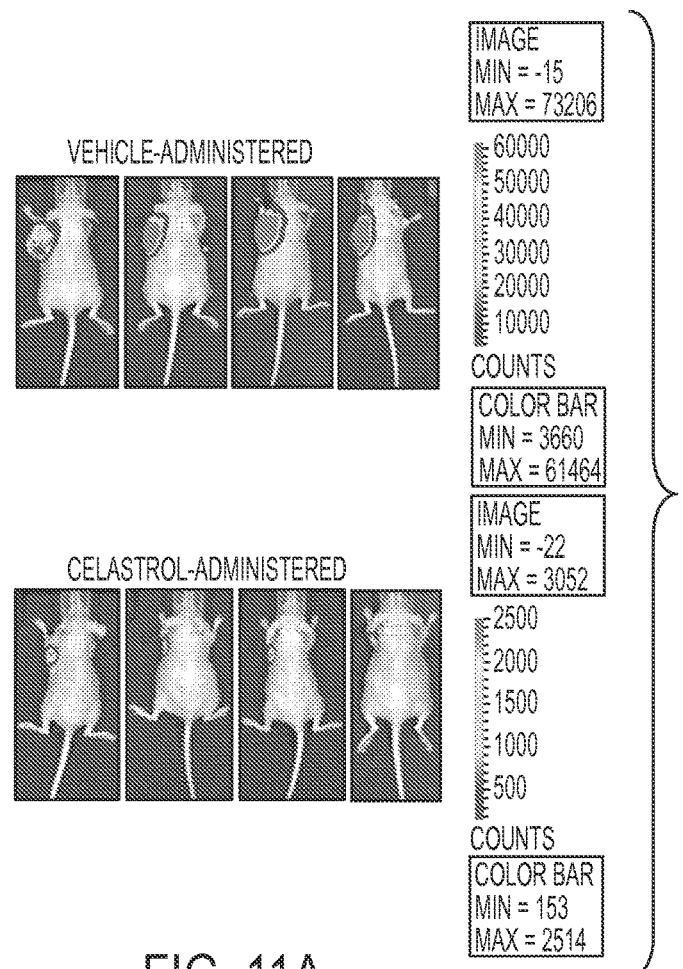
FIGS. 11A-D: Celastrol inhibited the growth of human MDA-MB-231 breast tumors in vivo.
Figure 11B:
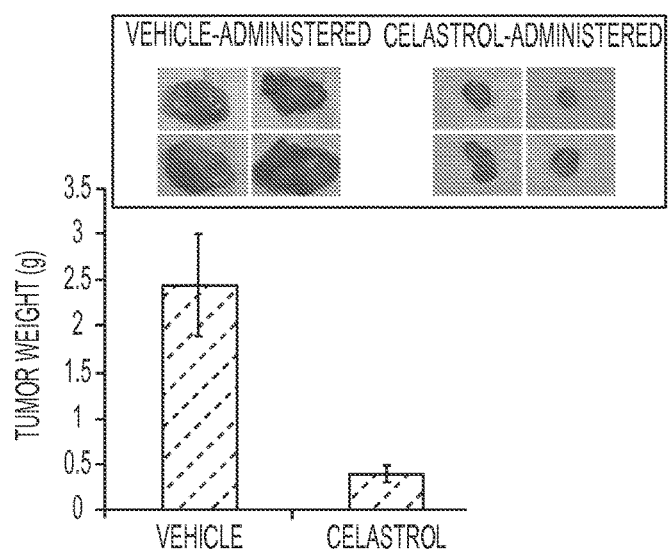
Figure 11C:
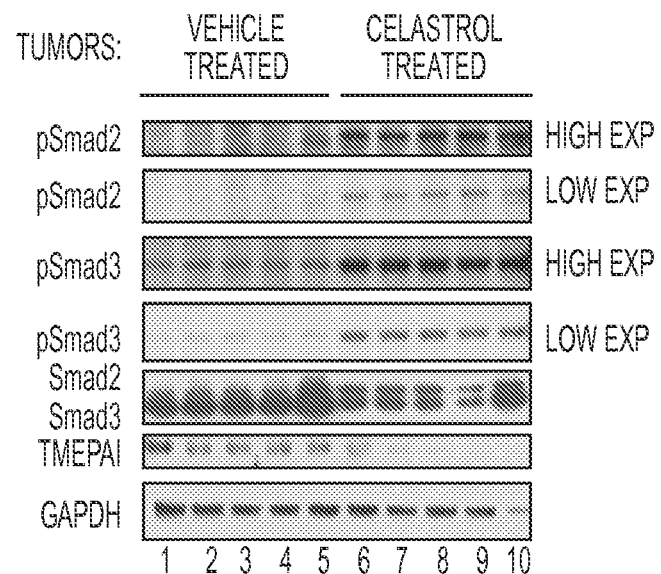
Figure 11D:
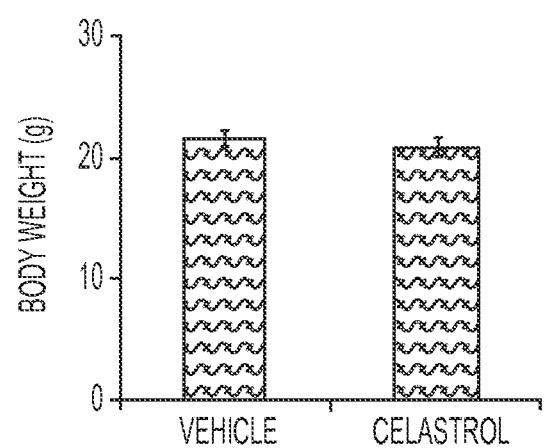
Figure 12A:
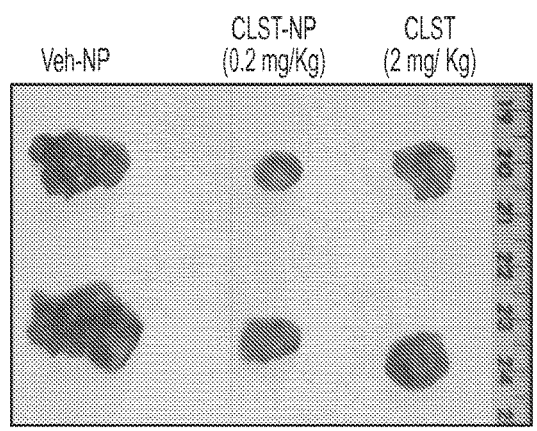
FIGS. 12A-D. Celastrol-loaded lecithin nanoparticles inhibited tumor growth in vivo.
Figure 12C:
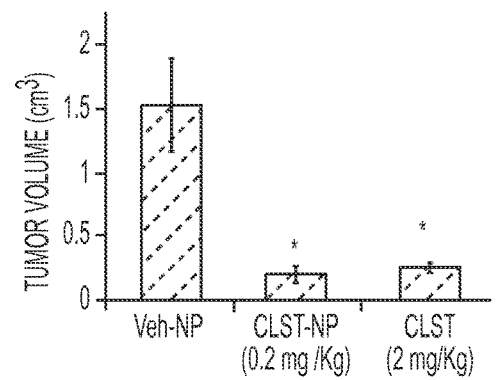
Figure 12B:
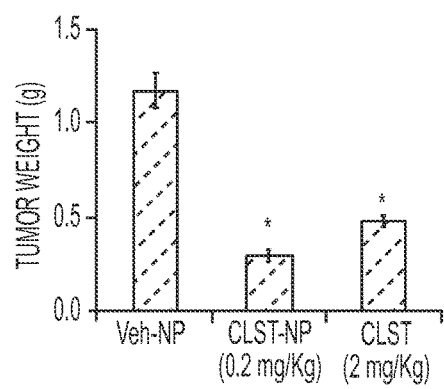
Figure 12D:
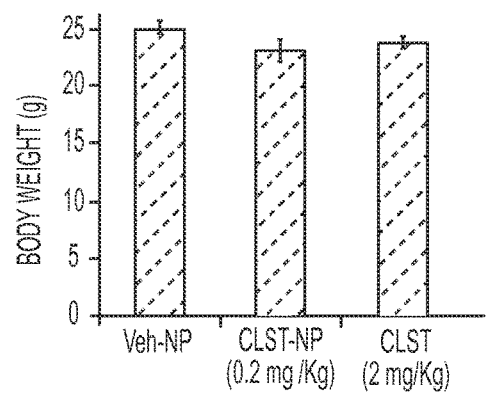

Pharmacological Inhibition of TMEPAI Expression Reduces Tumor Growth In Vivo. Celastrol reduced tumor burden in mice that were inoculated with aggressive MDA-MB-231 cells that expressed GFP-luciferase along with high endogenous TMEPAI levels. There is a large increase in luminescence signal (10000-60000 RLU) in the tumors that were treated with vehicle alone and celastrol treatment significantly blocked tumor growths (500-2500 RLU) in these mice (FIG. 11A). Compared to vehicle-treatment, celastrol treatment led to a ~6-fold reduction in tumor burden (FIG. 11B). In contrast, the total body weights of mice treated with vehicle and celastrol remained the same (FIG. 11D) suggesting that there are no toxic effects of celastrol at the dose given to mice. Celastrol treatment significantly elevated TGF-β signaling in the tumors since expression levels of phospho-Smad2 and 3 were increased and TMEPAI expression was reduced (FIG. 11C). Thus, these preclinical studies confirm that TMEPAI expressing breast cancers thrive by suppressing tumor suppressive TGF-β signaling and are therefore susceptible to pharmacological inhibition of TMEPAI expression by celastrol.

Celastrol Loaded Nanoparticles are Efficient in Tumor Targeting and Tumor Inhibition. Because of low aqueous solubility of celastrol (Log Po/w of 5.63), known systemic toxicity, a higher dose of tripterine than that of a solution can be achieved by suspending it in nanoparticles. Nanoparticle formulation will also enhance the bioavailability of insoluble hydrophobic drug (Merisko-Liversidge, 2008). The inventors prepared the solid lipid nanoparticles from lecithin-in-water emulsions encapsulated with celastrol, characterize them, and tested them in cell culture and animal studies to know the efficiency for tumor targeting and uptake of the drug. The end points are cell death in in vitro and animal well-being and tumor volume in vivo.

Unlike previous formulations of celastrol nanoparticles (Song, 2011; Huang, 2012), which used Tween 80 and deoxycholate as surfactants, the inventors used Tween 20 as a surfactant during the preparation and filtered through LIPEX™ Extruder to generate a homogeneous population of unilamellar liposomes ranging from ~50-100 nm with the appropriate filters to achieve maximum reduction in the liposomal size. This reduced size has more potential in extravasating the blood capillaries to targeting sites. The calculated entrapment efficiency of the celastrol into the nanoparticles (CLST-NP) was 91.8%.

As shown in FIGS. 12A-D, celastrol-loaded lecithin nanoparticles inhibited tumor growth in vivo. In fact, the 0.2 mg/kg celastrol containing liposomes (CLST-NP) were more effective than 2 mg/Kg celastrol alone (CLST) in reducing tumor size, tumor weight and tumor volume. Similarities in body weights of animals treated with vehicle or drugs indicate non-toxicity of CLST-NP and CLST at the doses administered.

Figure 13A:
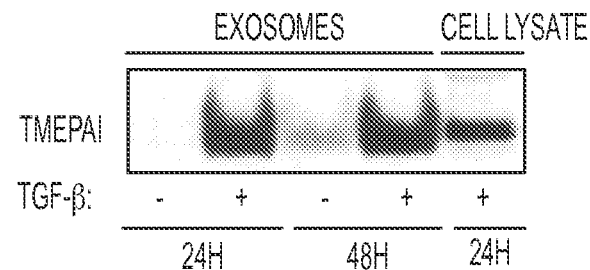
FIGS. 13A-B. Presence of TMEPAI in exosomes secreted by breast cancer cells into external medium.
Figure 13B:
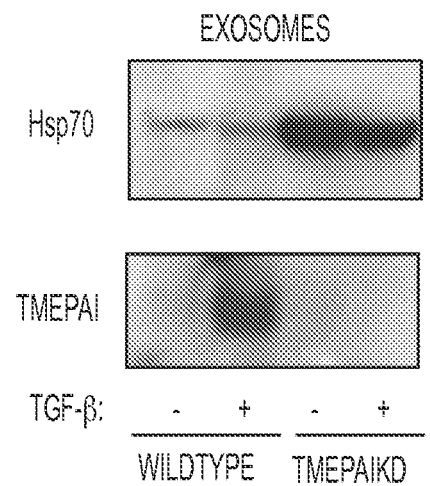

Release of TMEPAI Containing Exosomes by MDA-MB-231 Cells into Medium Suggests that TMEPAI is an Excellent Cancer Biomarker. Different types of membrane vesicles especially nanosized membrane vesicles, termed "exosomes" are secreted by many cell types under both physiological and pathological conditions, especially by tumor cells. These vesicles are formed either at the surface of a blebbing plasma membrane or inside internal cellular compartments (Denzer, 2000). The inventors tested whether triple negative breast cancer cells MDA-MB-231 that produce TMEPAI when stimulated by TGF-beta release this protein into extracellular medium in the form of exosomes. Isolated exosomes from culture medium of MDA-MB-231 cells that were treated with TGF-beta contained copious amounts of TMEPAI (FIG. 13A). In the absence of TMEPAI, there is more Hsp70 was present in the exosomes secreted by TMEPAI deficient cells (TMEPAIKD) (FIG. 13B). Since TMEPAI is a molecule found on most cancer cells, including breast, colon, prostate and lung cancers, but not on normal cells. TMEPAI can be used in blood tests to determine if a patient has cancer or residual cancer after treatment. TMEPAI could be used both as an early tumor marker as well as an advanced metastasis cancer marker.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

Moustakas A, Heldin C H. Non-Smad TGF-β signals. *J Cell Sci.* 2005; 118:3573-84.

Kang et al. New regulatory mechanisms of TGF-beta receptor function. *Trends Cell Biol.* 2009; 19:385-94.

Parvani et al. Noncanonical TGF-beta Signaling During Mammary Tumorigenesis. *J. Mammary Gland Biol Neoplasia* 2011; 16:127-46.

Xu et al. A novel androgenregulated gene, PMEPA1, located on chromosome 20q13 exhibits high level expression in prostate. *Genomics* 2000; 66:257-63.

Brunschwig et al. PMEPA1, a transforming growth factor-beta-induced marker of terminal colonocyte differentiation whose expression is maintained in primary and metastatic colon cancer. *Cancer Res.* 2003; 63:1568-75.

Bonafoux D, Lee W C. Strategies for TGF-beta modulation: a review of recent patents. Expert Opin Ther Pat. 2009; 19(12):1759-69.

Samarnthai et al., TMEPAI Gene Amplification in Triple Negative Breast Cancers. *Mod. Pathol.;* 23:70A, 2010.

Singha et al., Transforming growth factor-beta (TGF-beta)-inducible gene TMEPAI converts TGF-beta from a tumor suppressor to a tumor promoter in breast cancer. *Cancer Res.;* 70:6377-83, 2010.

Watanabe et al. TMEPAI, a transmembrane TGF-β-inducible protein, sequesters Smad proteins from active participation in TGF-β signaling. *Mol Cell.;* 37(1):123-34.4, 2010.

Gyorffy et al. An online survival analysis tool to rapidly assess the effect of 22,277 genes on breast cancer prognosis using microarray data of 1,809 patients. *Breast Cancer Res Treat.;* 123(3):725-31, 2010.

Merisko-Liversidge E M, Liversidge G G. Drug nanoparticles: formulating poorly water-soluble compounds. *Toxicol Pathol.* January; 36(1):43-8, 2008.

Song J, et al. Formulation and evaluation of celastrol-loaded liposomes. *Molecules* 13; 16(9):7880-92, 2011.

Huang et al., Preparation, characterization, and assessment of the antiglioma effects of liposomal celastrol. *Anticancer Drugs;* 23(5):515-24, 2012.

Denzer et al., Exosome: from internal vesicle of the multivesicular body to intercellular signaling device. *J Cell Sci* 113 Pt 19, 3365-3374, 2000.

The invention claimed is:

1. A method of inhibiting a cancer cell comprising (a) measuring transmembrane prostate androgen induced (TMEPAI) levels one or more cancer cells, and (b) contacting a cancer cell from step (a) found to overexpress TMEPAI as compared to a normal control cell with celastrol, wherein the cancer cell is a triple negative breast cancer cell.

2. The method of claim 1, further comprising contacting said cell with a second anti-cancer agent or therapy.

3. The method of claim 1, wherein said cancer cell is metastatic, recurrent or multi-drug resistant.

4. A method of treating a subject with cancer comprising (a) measuring transmembrane prostate androgen induced (TMEPAI) in cells of said cancer and (b) administering celastrol to the subject found to have cancer cells that overexpress TMEPAI as compared to a normal control cell, wherein the cancer is a triple negative breast cancer cell.

5. The method of claim 4, further comprising administering to said subject a second anti-cancer agent or therapy.

6. The method of claim 4, wherein said cancer is metastatic, recurrent or multi-drug resistant.

7. The method of claim 4, wherein said agent is administered intravenously, intra-arterially, subcutaneously, orally, intratumorally, locally or regionally to a tumor site, or systemically.

8. The method of claim 4, wherein the treating results in one or more of reduced tumor burden, slowing of tumor growth, increased length of survival, rendering an unresectable tumor resectable, or improvement of quality of life.

* * * * *